United States Patent
Li et al.

(10) Patent No.: US 11,833,212 B2
(45) Date of Patent: *Dec. 5, 2023

(54) LINKER PEPTIDE FOR CONSTRUCTING FUSION PROTEIN

(71) Applicant: AMPSOURCE BIOPHARMA SHANGHAI INC., Shanghai (CN)

(72) Inventors: Qiang Li, Shanghai (CN); Yuanli Li, Shanghai (CN); Si Chen, Shanghai (CN); Zhu Wang, Shanghai (CN); Zhao Dong, Shanghai (CN); Zirui Li, Shanghai (CN); Xinlu Ma, Shanghai (CN); Lu Yang, Shanghai (CN); Yongjuan Gao, Shanghai (CN); Yuncheng Zheng, Shanghai (CN); Naichao Sun, Shanghai (CN)

(73) Assignee: AMPSOURCE BIOPHARMA SHANGHAI INC., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/391,535

(22) Filed: Aug. 2, 2021

(65) Prior Publication Data

US 2022/0105193 A1 Apr. 7, 2022

Related U.S. Application Data

(63) Continuation of application No. 16/326,412, filed as application No. PCT/CN2016/106011 on Nov. 16, 2016, now Pat. No. 11,123,438.

(30) Foreign Application Priority Data

Aug. 19, 2016 (CN) .......................... 201610692679.4
Aug. 19, 2016 (CN) .......................... 201610694914.1

(51) Int. Cl.
| | |
|---|---|
| *A61K 47/65* | (2017.01) |
| *A61P 3/04* | (2006.01) |
| *A61P 3/10* | (2006.01) |
| *C07K 14/475* | (2006.01) |
| *C12N 15/62* | (2006.01) |
| *C12N 15/63* | (2006.01) |
| *C07K 19/00* | (2006.01) |
| *C07K 14/54* | (2006.01) |
| *C07K 14/755* | (2006.01) |
| *C07K 16/06* | (2006.01) |
| *C07K 16/28* | (2006.01) |
| *C07K 16/46* | (2006.01) |
| *C12N 15/85* | (2006.01) |

(52) U.S. Cl.
CPC ............... *A61K 47/65* (2017.08); *A61P 3/04* (2018.01); *A61P 3/10* (2018.01); *C07K 14/475* (2013.01); *C07K 14/5418* (2013.01); *C07K 14/755* (2013.01); *C07K 16/065* (2013.01); *C07K 16/2809* (2013.01); *C07K 16/2887* (2013.01); *C07K 16/468* (2013.01); *C07K 19/00* (2013.01); *C12N 15/62* (2013.01); *C12N 15/63* (2013.01); *C12N 15/85* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,818,679 A | 4/1989 | Chasin et al. |
| 6,103,501 A | 8/2000 | Boime et al. |
| 6,225,449 B1 | 5/2001 | Boime |
| 7,189,827 B2 | 3/2007 | Feige |
| 8,163,889 B2 | 4/2012 | Kim et al. |
| 8,304,224 B2 | 11/2012 | Lövgren |
| 9,023,791 B2 | 5/2015 | Boettcher et al. |

(Continued)

FOREIGN PATENT DOCUMENTS

| | | |
|---|---|---|
| CN | 1290301 A | 4/2001 |
| CN | 1889937 A | 1/2007 |

(Continued)

OTHER PUBLICATIONS

U.S. Appl. No. 16/604,088, filed Oct. 9, 2019, now published as US20200157344A), May 21, 2020, Amsource Biopharma Shanghai Inc.
Gerhard Dickneite, Prothrombin complex concentrate versus recombinant factor VIIa for reversal of coumarin anticoagulation, Thrombosis Research (2007) 119, 643-651, Germany.
Gary E. Gilbert and Diane Drinkwater, Specific Membrane Binding of Factor VIII Is Mediated by O-Phospho-L-serine, a Moiety of Phosphatidylserine, Biochemistry 1993, 32, 9577-9585. Boston, Massachusetts.

(Continued)

*Primary Examiner* — Thomas S Heard
(74) *Attorney, Agent, or Firm* — Finnegan, Henderson, Farabow, Garrett & Dunner LLP

(57) ABSTRACT

A linker peptide for constructing a fusion protein. The linker peptide comprises a flexible peptide and a rigid peptide. The flexible peptide consists of one or more flexible units. The rigid peptide consists of one or more rigid units. The flexible unit comprises two or more amino acid residues selected from Gly, Ser, Ala, and Thr. The rigid unit comprises a human chorionic gonadotropin β-subunit carboxy-terminal peptide (CTP) bearing a plurality of glycosylation sites. The linker peptide can more effectively eliminate mutual steric hindrance of two fusion molecules, decreasing a reduction/loss of polymerization or activity resulting from improper folding of an active protein or a conformational change. On the other hand, the negatively charged, highly sialylated CTP can resist renal clearance, further prolonging a half-life of a fused molecule and enhancing bioavailability of a fused protein. Furthermore, a protective effect of a glycosylated side chain CTP can lower the protease sensitivity of the linker peptide, making a linker region of the fusion protein less degradable.

20 Claims, 8 Drawing Sheets

Specification includes a Sequence Listing.

(56) References Cited

U.S. PATENT DOCUMENTS

| | | | |
|---|---|---|---|
| 9,266,935 B2 | 2/2016 | Boettcher et al. |
| 10,010,622 B2 | 7/2018 | Dumont et al. |
| 10,287,564 B2 | 5/2019 | Hong et al. |
| 2001/0012628 A1 | 8/2001 | Agarwal et al. |
| 2003/0211580 A1 | 11/2003 | Lustbader |
| 2005/0250185 A1 | 11/2005 | Murphy et al. |
| 2007/0129298 A1 | 6/2007 | Krebber et al. |
| 2009/0042784 A1 | 2/2009 | Krarup |
| 2010/0081614 A1 | 4/2010 | Fares et al. |
| 2015/0203558 A1 | 7/2015 | Fares et al. |
| 2015/0353911 A1 | 12/2015 | Salas et al. |
| 2016/0115467 A1 | 4/2016 | Salas |
| 2019/0184026 A1 | 6/2019 | Li et al. |
| 2019/0365867 A1 | 12/2019 | Li et al. |
| 2020/0157185 A1 | 5/2020 | Gao et al. |

FOREIGN PATENT DOCUMENTS

| | | |
|---|---|---|
| CN | 101010338 A | 8/2007 |
| CN | 1802386 B | 12/2010 |
| CN | 102625811 A | 8/2012 |
| CN | 102802657 A | 11/2012 |
| CN | 103328502 A | 9/2013 |
| CN | 103539860 A | 1/2014 |
| CN | 103539861 A | 1/2014 |
| CN | 103539868 A | 1/2014 |
| CN | 103539869 A | 1/2014 |
| CN | 103649127 A | 3/2014 |
| CN | 103827142 A | 5/2014 |
| CN | 103945871 A | 7/2014 |
| CN | 104024273 B | 9/2014 |
| CN | 104039831 A | 9/2014 |
| CN | 104114183 A | 10/2014 |
| CN | 104427994 A | 3/2015 |
| CN | 104519897 A | 4/2015 |
| CN | 104519912 A | 4/2015 |
| CN | 104693270 A | 6/2015 |
| CN | 104903352 A | 9/2015 |
| CN | 105153313 A | 12/2015 |
| CN | 104774269 | 2/2016 |
| CN | 103897064 B | 5/2016 |
| CN | 105753945 A | 7/2016 |
| CN | 106256835 A | 12/2016 |
| CN | 106279436 A | 1/2017 |
| CN | 106279437 A | 1/2017 |
| CN | 106317226 B | 9/2017 |
| CN | 107474138 | 12/2017 |
| CN | 110028587 | 7/2019 |
| EA | 005404 B1 | 2/2005 |
| EA | 201291480 | 9/2013 |
| EP | 1624891 B1 | 8/2009 |
| JP | 2014-522838 | 9/2014 |
| KR | 2010-0099179 | 9/2010 |
| KR | 10-1027427 | 4/2011 |
| RU | 2312868 C2 | 12/2007 |
| WO | WO2003/011213 | 2/2003 |
| WO | WO2003/061712 | 7/2003 |
| WO | WO2004110472 | 12/2004 |
| WO | WO2005000892 | 1/2005 |
| WO | WO 2005058953 A2 | 6/2005 |
| WO | WO2005091944 A2 | 10/2005 |
| WO | WO2006050247 A2 | 10/2005 |
| WO | WO2005113606 | 12/2005 |
| WO | WO2006/028595 | 3/2006 |
| WO | WO2006/028714 | 3/2006 |
| WO | WO2006053301 | 5/2006 |
| WO | WO2006/065582 | 6/2006 |
| WO | WO2007090584 | 8/2007 |
| WO | WO2008121563 A2 | 10/2008 |
| WO | WO2009149171 | 12/2009 |
| WO | WO2010042747 | 4/2010 |
| WO | WO2010084169 A2 | 7/2010 |
| WO | WO2010129503 | 11/2010 |
| WO | WO2010129600 | 11/2010 |
| WO | WO2010142665 | 12/2010 |
| WO | WO2011071783 A1 | 6/2011 |
| WO | WO2011092234 | 8/2011 |
| WO | WO2011130417 A2 | 10/2011 |
| WO | WO2012010553 A1 | 1/2012 |
| WO | WO2012066075 A1 | 5/2012 |
| WO | WO2012158704 | 11/2012 |
| WO | WO2012170438 A2 | 12/2012 |
| WO | WO2012175751 | 12/2012 |
| WO | WO2013049234 | 4/2013 |
| WO | WO2013049247 | 4/2013 |
| WO | WO2013096386 A | 6/2013 |
| WO | WO2013100702 | 7/2013 |
| WO | WO2013121416 | 8/2013 |
| WO | WO2013152351 A2 | 10/2013 |
| WO | WO2013185114 | 12/2013 |
| WO | WO2013188181 | 12/2013 |
| WO | WO2014026954 A1 | 2/2014 |
| WO | WO2014037373 | 3/2014 |
| WO | 02014/052490 | 4/2014 |
| WO | WO2014106015 A | 7/2014 |
| WO | WO2016114633 | 7/2016 |
| WO | WO2017074123 | 5/2017 |

OTHER PUBLICATIONS

Ying Tang, Ning Jiang, Cushrow Parakh, and Donald Hilvert, Selection of Linkers for a Catalytic Single-chain Antibody Using Phage Display Technology, The Journal of Biological, vol. 271, No. 26, Issue of Jun. 29, pp. 15682-15686, 1996, USA.

Ryoichi Arai, Hiroshi Ueda, Atsushi Kitayama, Noriho Kamiya, and Teruyuki Nagamune, Design of the linkers which effectively separate domains of a bifunctional fusion protein, Protein Engineering vol. 1, No. 8, pp. 529-532, 2001, Oxford University Press.

Dahai Luo, Na Wei, Danny, N. Doan, Prasad N. Paradkar, Yuwen Chong, Andrew D, Davidson, Masayo Kotaka, Julien Lescar, and Subhash G. Vasudevan, Flexibility between the Protease and Helicase Domains of the Dengue Virus NS3 Protein Conferred by the Linker Region and Its Functional Implications, The Journal of Biological Chemistry vol. 284, No. 24, pp. 18817-18827, Jun. 11, 2010, USA.

Fuad A. Fares, Nobuhiko Suganuma, Keiji Nishimori, Philip S. Lapolt, Aaron J.W. Hsueh, and Irving Boime, Design of a long-acting follitropin agonist by fusing the C-terminal sequence of the chorionic gonadotropin ß submit to the follitropin ß subunit, Proc. Natl. Acad. Sci, USA vol. 89, pp. 4304-4308, May 1992, Medical Sciences.

Joe Salas, Tongyao Liu, Qi LU, John D. Kulman, Tamera Ashworth, Elena Kistanova, Nancy Moore, Glenn F. Pierce, Haiyan Jiang, Robert Peters, Enhanced Pharmacokinetics of Factor VIIa as a Monomeric Fc Fusion, Thrombosis Research 135 (2015) 970-976, Elsevier Ltd.

H. Uchida, S. Bana, M. Wada, K. Matsumoto, M. Ikeda, N. Naito, E. Tanaka, and M. Honjo, Analysis of binding properties between 20 kDa human growth hormone (hGH) and hGH receptor (hGHR): the binding affinity for hGHR extracellular domain and mode of receptor dimerization, Journal of Molecular Endocrinology (1999) 23, 347-353, 1999 Society for Endocrinology, Great Britain.

Li, Jianfang et al., "Design of Linker Peptides and Its Application in Fusion Protein", 2015, *Journal of Food Science & Biotechnology*, 34:1121-1127.

International Search Report for International Application No. PCT/CN2016/106011, dated Feb. 28, 2017.

Written Opinion of the International Searching Authority for International Application No. PCT/CN2016/106011, dated Jan. 28, 2017.

Gang Li et al., Construction of a Linker Library with Widely Controllable Flexibility for Fusion Protein Design, *Appl. Microbiol Biotechnol.*, vol. 100, pp. 215-225, 2016.

Joshua S Klein et al., Design and Characterization of Structured Protein Linkers with Differing Flexibilities, *Protein Engineering*, vol. 27, No. 10, pp. 325-330, 2014.

Skosyrev, V S et al. "The Dependence of Stability of the Green Fluorescent Protein—Obelin Hybrids on the Nature of Their Constituent Modules and the Structure of the Amino Acid Linker", Russian Journal of Bioorganic Chemistry 27, 323-329 (2001).

(56) References Cited

OTHER PUBLICATIONS

Treetharnmathurot B et al, "Effect of PEG molecular weight and linking chemistry on the biological activity and thermal stability of PEGylated trypsin", Int J Pharma, 2008, 357:252-259.
Wen D et al, "Discovery and Investigation of O-Xylosylation in Engineered Proteins Containing a (GGGGS)n Linker", Anal. Chem., 2013, 85:4805-4812.
International Search Report for International Application No. PCT/CN2017/079871, dated Jul. 7, 2017.
Written Opinion of the International Searching Authority for International Application No. PCT/CN2017/079871, dated Jul. 7, 2017.
Turecek P.L. et al., "BAX 855, a PEGylated rFVIII product with prolonged half-life", Hamostaseologie, 2012, 32:S29-S38.
Moore D D, "Sister Act", Science, 2007, 316:1436-1438.
Beenken et al, "The FGF family: biology, pathophysiology and therapy", Nature Reviews Drug Discover, 2009, 8_235.
Yie J et al, "FGF21 N- and C-termini play different roles in receptor interaction and activation", FEBS Lett, 2009, 583(1):19-24.
Micanovic R et al., "Different Roles of N- and C-Termini in the Functional Activity of FGF21", J Cell Physiol, 2009, 219(2):227-234.
Kharitonenkov A et al, "FGF-21 as a novel metabolic regulator", J Clin Invest, 2005, 115(6): 1627-1635.
Coskun T et al, "Fibroblast growth factor 21 corrects obesity in mice", Endocrinology, 2008, 149(12):6018-6027.
Xu J et al, "Fibroblast Growth Factor 21 Reverses Hepatic Steatosis, Increases Energy Expenditure, and Improves Insulin Sensitivity in Diet-Induced Obese Mice", Diabetes, 2009, 58, 250-259.
Berglund ED et al, "Fibroblast growth factor 21 controls glycemia via regulation of hepatic glucose flux and insulin sensitivity", Endocrinology, 2009,150(9):4084-4093.
Xu J et al, "Acute glucose-lowering and insulin-sensitizing action of FGF21 in insulin-resistant mouse models—association with liver and adipose tissue effect", Am J Physiol Endocrinol Metab, 2009, 297(5):E1105-1114.
Kharitonenkov A et al, "The metabolic state of diabetic monkeys is regulated by fibroblast growth factor-21", Endocrinology, 2007,148(2):774-781.
Hecht R et al, "Rationale-based engineering of a potent long-acting FGF21 analog for the treatment of type 2 diabetes", PLoS One, 2012, 7: e49345.
Shields RL et al, "High Resolution Mapping ofthe Binding Site on Human IgG1 for FchI, FchII, FchIII, and FcRn and Design of IgG1 Variants with Improved Binding to the FcgR", J Biol Chem, 2001, 276:6591-604.
Jefferis R et al, "IgG-Fc-mediated effector functions: molecular definition of interaction sites for effector ligands and the role of glycosylation", Immunol Rev, 1998, 163_ 59-76.
Hinton P R et al., "An Engineered Human IgG1 Antibody with Longer Serum Half-Life", J Immunol, 2006, 176_346-356
Datta-Mannan A et al, "Influence of improved FcRn binding on the subcutaneous bioavailability of monoclonal antibodies in cynomolgus monkeys", MAbs. Taylor & Francis, 2012, 4(2):267-273.
Collins PW et al., "Recombinant long-acting glycoPEGylated factor IX in hemophilia B: a multinational randomized phase 3 trial", Blood, 2014, 124(26):3880-3886.
Hart G et al., "FVIIa-CTP and FIX-CTP are novel long-acting coagulation factors with prolonged hemostatic activity in hemophilic animal models: PO-TU-025", Haemophilia, 2012, 18.
Peters RT et al, "Prolonged activity of factor IX as a monomeric Fc fusion protein", Blood, 2010, 115(10):2057-2064.
Roopenian et al, "FcRn: the neonatal Fc receptor comes of age", Nat Rview Immunology, 2007, 7:715-725.
Broze et al, "Purification and properties of human coagulation factor VII", J Biol Chem, 1980, 255: 1242-1247.
Golor G et al, "Safety and pharmacokinetics of a recombinant fusion protein linking coagulation factor VIIa with albumin in healthy volunteers", J Thromb Haemost, 2013, 11:1977-85.
Weimer T et al., "Prolonged in-vivo half-life of factor VIIa by fusion to albumin", Thromb Haemost, 2008, 99: 659-667.
Ljung R et al, "40K glycoPEGylated, recombinant FVIIa: 3-month, doubleblind, randomized trial of safety, pharmacokinetics and preliminary efficacy in hemophilia patients with inhibitors", J Thromb Haemost, 2013, 11(7):1260-1268
Hinton P R et al, "Engineered Human IgG Antibodies with Longer Serum Half-lives in Primates", J Biol Chem, 2004, 279:6213-6216.
Hagen FS et al, "Characterization of a cDNA coding for human factor VII", Proc Natl Acad Sci USA, 1986, 83(8):2412-2416.
Hedner U et al, "Use of human factor VIIa in the treatment of two hemophilia A patients with high-titer inhibitors", J Clin Invest, 1983, 71:1836-1841.
Kisiel et al, "Enzymological aspects of blood coagulation", Behring Inst Mitt, 1983, 73:29-42.
Pedersen AH et al, "Autoactivation of human recombinant coagulation factor VII", Biochemistry, 1989, 28:9331-9336.
Bjoern S et al, "Activation of coagulation factor VII to VIIa", Res Disclosure, 1986, 269:564-565.
Dong J Q et al, "Pharmacokinetics and pharmacodynamics of PF-05231 023, a novel long-acting FGF21 mimetic, in a first-in-human study", Br J Clin Pharmacol, 2015, 80:1051-1063.
Dutchak P A et al, "Fibroblast Growth Factor-21 Regulates PPARg Activity and the Antidiabetic Actions of Thiazolidinediones", Cell, 2012, 148:556-567.
Gaich G et al, "The Effects of LY2405319, an FGF21 Analog, in Obese Human Subjects with Type 2 Diabetes", Cell Metabollism, 2013, 18:333-340
Knudsen L B, "Glucagon-like Peptide-1: The Basis of a New Class of Treatment for Type 2 Diabetes", J Med Chem, 2004, 47:4128-4134.
Lin Z et al, "Fibroblast Growth Factor 21 Prevents Atherosclerosis by Suppression of Hepatic Sterol Regulatory Element-Binding Protein-2 and Induction of Adiponectin in Mice", Circulation, 2015, 131 :1861-1871.
Neidigh J W et al, "Exendin-4 and Glucagon-like-peptide-1: NMR Structural Comparisons in the Solution and Micelle-Associated States", Biochemistry, 2001, 40:13188-13200.
Petit J M et al, "GLP-1 receptor agonists in NAFLD", Diabetes & Metab, 2017, 43: S28-S33.
Radaelli M G et al, "NAFLD/NASH in patients with type 2 diabetes and related treatment options", J Endocrinno Invest, 2018, 41:509-521.
Wu X et al, "Separating mitogenic and metabolic activities of fibroblast growth factor 19 (FGF19)", Proc Natl Acad Sci USA, 2010, 107:14158-14163.
Calo et al, "Enhancing the longevity and in vivo potency of therapeutic proteins: The power of CTP", Precision Medicine, 2015, 2:e989.
International Search Report for International Application No. PCT/CN2016/106012, dated May 22, 2017.
International Search Report for International Application No. PCT/CN2017/079872, dated July 5, 2017.
Doron et al., Enhancing the longevity and in vivo potency of therapeutic proteins: The power of CTP, Precision Medicine, 2015, 2: e989.
Maeda Y, et al. Engineering of Functional Chimeric Protein G-Vargula Luciferase, Anal Biochem. 1997, 249(2):147-52.
Orlando M., Modification of proteins and low molecular weight substances with hydroxyethyl starch (HES), Inauguraldissertation, Giesen, 2003, p. 166, p. 15.
Chen X, Zaro J L, Shen WC. Fusion Protein Linkers: Property, Design and Functionality, Adv Drug Deliv Rev, 2013, 65(10): 1357-1369.
Supplementary European Search Report for EP17840761, dated Jan. 20, 2021

LINKER PEPTIDE FOR CONSTRUCTING FUSION PROTEIN

CROSS-REFERENCE TO RELATED APPLICATIONS

This application is a continuation of application Ser. No. 16/326,412, filed on Feb. 19, 2019, which is a United States national stage entry under 35 U.S.C. § 371 of International Application No. PCT/CN2016/106011, filed on Nov. 16, 2016, which claims priority to Chinese Patent Application Nos. 201610692679.4, filed on Aug. 19, 2016, and 201610694914.1, filed on Aug. 19, 2016. The contents of these applications are each incorporated herein by reference in their entirety.

SEQUENCE LISTING

Please insert the sequence listing, filed herewith in electronic format, into the application before the claims.

FIELD OF THE INVENTION

The present invention relates to the field of fusion proteins and, more specifically, to a peptide linker for the construction of fusion proteins.

BACKGROUND

In recent two decades, protein fusion technology has been widely used in the construction of bifunctional antibodies, bifunctional enzymes, and bifunctional proteins. However, a variety of problems have been encountered in the construction of fusion proteins. For example, proteins that fold correctly during expression alone do not fold properly in the fusion protein; the active site is blocked after fusion due to the short distance between the two fused proteins; the fusion protein molecule is easily degraded by proteases when it cannot fold properly or when its conformation has changed; the protein catalytic domain with certain flexibility loses its original function after fusion; and so on. The emergence of these problems often leads to reduction or even complete loss of the activity of the fusion proteins. It is generally believed that the activity of the original protein molecule will decrease to a certain extent after the protein molecule is constructed in the fusion protein. A favorable fusion protein is the one that keeps more than 50% activity of the original protein molecule(s). In order to solve the above problems, researchers conducted many studies and explorations on the design and construction of fusion proteins to improve the activity of fusion proteins. such as changing the linking order of the fused proteins, changing different fusion sites, using different fusion partners, or using a peptide linker, etc.

Compared with other fusion strategies, the use of a peptide linker has a variety of advantages. First, the amino acids that make up the peptide linker are diverse (20 common amino acids). The length of the peptide linker is also an important tunable parameter, which can lead to rich diversity of peptide linkers ($20^n$, n is the number of amino acid residues of the peptide linker). The peptide linkers are easy for bioengineering modifications. Second, the peptide linker provides certain spatial spacing, such that the two fused proteins fold correctly without interfering with each other. Third, the peptide linker can also provide more interaction possibilities for two fused proteins, promoting synergic interactions.

There are currently two kinds of commonly used peptide linkers, helical rigid peptide linkers (such as A(EAAAK)$_n$A (SEQ ID NO: 34)) and flexible peptide linkers comprising less hydrophobic and less charged amino acids. The helical rigid peptide linkers can effectively separate different functional regions of the fusion proteins. Examples of flexible peptide linkers include the (GGGGS)$_3$ sequence (SEQ ID NO: 35) that Huston designed. In addition, it has been reported that the carboxyl terminal peptide (hereinafter referred to as CTP) of human chorionic gonadotropin (HCG) beta chain can be used as a peptide linker alone, and is mainly used to link different subunits of the same protein. For example, CTP is used as a peptide linker between the beta and alpha subunits of follicle stimulating hormone, as disclosed in Chinese Patent Nos. CN103539860A, CN103539861A, CN103539868A and CN103539869A. In WO2005058953A2, CTP is used as a peptide linker in the fusion protein, linking the glycoprotein beta and alpha subunits. However, because CTP has the effect of prolonging the in vivo half-life of certain proteins, it has been primarily disclosed as a half-life prolonging moiety in the fusion proteins in many other patents. The half-life prolonging moiety can optionally choose CTP, immunoglobulin Fc, or other fusion partners with similar half-life prolonging function.

A number of literatures have reported the effects of the peptide linker sequences on the construction and expression of fusion proteins. For example, in the construction of the single chain antibody 1F7, it was found that using a conventional Genex212 peptide linker (GSTSGSGKSSEGKG (SEQ ID NO: 36)) to link the light and heavy chains did not achieve the original catalytic activity of the protein and the fusion protein was unstable. After a library of 18 amino acid residues with random sequences was constructed and screened, catalytically active single chain antibodies were obtained (Tang Y et al., 1996, J Biol Chem., 271:15682-15686). In studying the helical peptide, Arai et al. found that the fluorescence resonance energy transfer from EBFP to EGFP reduced as the length of the peptide linker increased, suggesting that increasing the linker length could effectively separate the two functional regions (Arai R. et al., 2001, Protein Eng., 14:529-532). In addition, in studying dengue virus NS2B protein, Luo et al. found that inserting a glycine residue between the original sites 173 and 174, or replacing proline 174 with glycine, resulted in a significant decrease in protein activity of both the N- and C-terminal proteins. This indicated that the length and rigidity of the native peptide linker were the result of long-term evolution, and were of great significance to the function of the natural fusion proteins (Luo D. et al., 2010, J Biol Chem., 285:18817-18827). The N-terminus of the NS2B protein was a serine protease, the C-terminus was a RNA helicase, and the peptide linker between them had 11 amino acid residues.

The present inventors found that the length and amino acid composition of the peptide linker, the presence or absence of glycosylation sites, the compatibility between the peptide linker and the two active molecules, and other factors, could affect the function and stability of the fusion proteins. The inventors believe that the peptide linker should have the following characteristics: 1) can make the linked proteins fold effectively into proper conformations, does not cause molecular dynamics change, and preferably comprises non-immunogenic natural amino acids. 2) should have the ability to prevent protease attack. 3) should try to avoid mutual impacts of the two fused proteins on each other.

In the absence of clear guidelines for the design of peptide linkers, the present inventors have developed new peptide linkers for the construction of fusion proteins, based on the inventors' long-term research experience, particularly those in studying Fc fusion proteins. Amazingly, the peptide linkers have advantage for maintaining the biological activity of proteins or polypeptides and have broad applicability and portability.

DESCRIPTION OF THE INVENTION

The object of the present invention is to provide a novel peptide linker for constructing fusion proteins.

The first aspect of the present invention provides a peptide linker. The peptide linker comprises a flexible peptide and a rigid peptide. The flexible peptide consists of one or more flexible units, and the rigid peptide consists of one or more rigid units, wherein the flexible unit comprises two or more amino acid residues selected from Gly, Ser, Ala and Thr, and the rigid unit comprises the carboxyl terminal peptide (CTP) of human chorionic gonadotropin subunit.

Preferably, the peptide linker is glycosylated. More preferably, the glycosylation site is located on CTP. Much more preferably, the glycosylation process is accomplished by expression in mammalian cells, such as Chinese hamster ovary cells, or other expression hosts having a suitable glycosylation modification system.

Further, the rigid peptide in the peptide linker of the present invention is located at the N-terminus or C-terminus of the flexible peptide. Preferably, the rigid peptide is located at the C-terminus of the flexible peptide. Specifically, the structural formula of the peptide linker of the present invention can be represented as F-R or R-F, wherein F and R represent the flexible peptide and the rigid peptide, respectively. Further, the flexible peptide preferably comprises 1, 2, 3, 4 or 5 flexible units, and the rigid peptide preferably comprises 1, 2, 3, 4 or 5 rigid units.

More preferably, the flexible unit comprises two or more G and S residues. Much more preferably, the amino acid sequence of the flexible unit has the general formula $(GS)_a(GGS)_b(GGGS)_c(GGGGS)_d$ (SEQ ID NO: 37), wherein a, b, c and d represent the number of structural units composed of G and S residues, and are integers greater than or equal to 0, and a+b+c+d≥1.

Illustratively, each flexible unit is represented by $F_i$ and i=1, 2, 3, 4, 5, ... n. In some embodiments of the invention, the flexible peptide preferably comprises, but is not limited to the following flexible units:

```
(i) F1:
                                        (SEQ ID NO: 21)
GSGGGSGGGGSGGGGS;

(ii) F2:
                                        (SEQ ID NO: 22)
GSGGGGSGGGGSGGGGSGGGGSGGGGS;

(iii) F3:
                                        (SEQ ID NO: 23)
GSGGGGSGGGGSGGGGSGGGGSGGGGSGGGGSGGGGS;

(iv) F4:
                                        (SEQ ID NO: 24)
GSGGGGSGGGGSGGGGS;

(v) F5:
                                        (SEQ ID NO: 25)
GGGSGGGSGGGSGGGSGGGS;

(vi) F6:
                                        (SEQ ID NO: 26)
GGSGGSGGSGGS.
```

The rigid unit is selected from the full length or fragment sequence of the C-terminal amino acids 113 to 145 of human chorionic gonadotropin β subunit. Specifically, the rigid unit comprises the amino acid sequence of SEQ ID no: 1 or its truncated form.

Preferably, CTP contains at least 2 glycosylation sites. For example, in a preferred embodiment of the present invention, CTP contains 2 glycosylation sites. Illustratively, CTP contains the N-terminal 10 amino acids of SEQ ID no: 1, i.e. SSSS*KAPPPS* (residues 6-15 of SEQ ID NO: 1), or CTP contains the C-terminal 14 amino acids of SEQ ID no: 1, i.e. S*RLPGPS*DTPILPQ (residues 20-33 of SEQ ID NO: 1). For another example, in another embodiment of the present invention, CTP contains 3 glycosylation sites. Illustratively, CTP contains the N-terminal 16 amino acids of SEQ ID no: 1, i.e. SSSS*KAPPPS*LPSPS*R (residues 6-21 of SEQ ID NO: 1). For other examples, in other embodiments of the present invention, CTP contains 4 glycosylation sites. Illustratively, CTP contains 28, 29, 30, 31, 32, or 33 amino acids, starting from position 113, 114, 115, 116, 117, or 118 and ending at position 145 of the human chorionic gonadotropin beta subunit. Specifically, CTP contains the N-terminal 28 amino acids of SEQ ID no: 1, i.e. SSSS*KAPPPS*LPSPS*RLPGPS*DTPILPQ (residues 6-33 of SEQ ID NO: 1). In this text, * represents a glycosylation site. Each possibility represents a separate embodiment of the present invention.

In other embodiments, the rigid units provided by the present invention have at least 70% amino acid sequence identity to native CTP. In other embodiments, the rigid units provided by the present invention have at least 80% amino acid sequence identity to native CTP. In other embodiments, the rigid units provided by the present invention have at least 90% amino acid sequence identity to native CTP. In other embodiments, the rigid units provided by the present invention have at least 95% amino acid sequence identity to native CTP.

Illustratively, each rigid unit is represented by $R_i$ and i=1, 2, 3, 4, 5, ..., n. The rigid peptides described in some embodiments of the present invention may preferably comprise, but are not limited to, the following CTP rigid units.

```
(i) R1:
                                        (SEQ ID NO: 27)
SSSSKAPPPSLPSPSRLPGPSDTPILPQ;

(ii) R2:
                                        (SEQ ID NO: 28)
PRFQDSSSSKAPPPSLPSPSRLPGPSDTPILPQ;

(iii) R3:
                                        (SEQ ID NO: 29)
SSSSKAPPPS;

(iv) R4:
                                        (SEQ ID NO: 30)
SRLPGPSDTPILPQ;

(v) R5:
                                        (SEQ ID NO: 31)
SSSSKAPPPSLPSPSR.
```

The rigid peptides of the present invention may further comprise two or three of the above CTP rigid units. In one embodiment of the present invention, the rigid peptide comprises two R3 rigid units: SSSSKAPPPSSSSSKAPPPS (SEQ ID NO: 32) (represented as R3R3). In another embodiment, the rigid peptide comprises three R4 rigid units:

```
                                        (SEQ ID NO: 33)
SRLPGPSDTPILPQSRLPGPSDTPILPQSRLPGPSDTPILPQ
    (represented as R4R4R4).
```

In some preferred embodiments of the invention, the peptide linker has the amino acid sequence as shown in SEQ ID no: 2

```
(GSGGGGSGGGGSGGGGSGGGGSGGGGSSSSSKAPPPSLPSPSRLPGPSD
TPILPQ)
(represented as F2-R1).
```

In another preferred embodiment of the present invention, the peptide linker has the amino acid sequence as shown in SEQ ID no: 3

```
(GSGGGSGGGGSGGGGSPRFQDSSSSKAPPPSLPSPSRLPGPSDTPILPQ)
(represented as F1-R2).
```

In another preferred embodiment of the present invention, the peptide linker has the amino acid sequence as shown in SEQ ID no: 4

```
(GSGGGGSGGGGSGGGGSSSSSKAPPPSLPSPSRLPGPSDTPILPQ)
(represented as F4-R1).
```

In another preferred embodiment of the present invention, the peptide linker has the amino acid sequence as shown in SEQ ID no: 5

```
    (GGGSGGGSGGGSGGGSGGGSSSSSKAPPPSLPSPSR)
    (represented as F5-R5).
```

In another preferred embodiment of the present invention, the peptide linker has the amino acid sequence as shown in SEQ ID no: 6

```
    GSGGGSGGGGSGGGGSSSSSKAPPPSSSSSKAPPPS)
    (represented as F4-R3R3).
```

In another preferred embodiment of the present invention, the peptide linker has the amino acid sequence as shown in SEQ ID no: 7

```
(GGSGGSGGSGGSSRLPGPSDTPILPQSRLPGPSDTPILPQSRLPGPSDT
PILPQ)
(represented as F6-R4R4R4).
```

Yet another aspect of the invention provides a fusion protein containing the peptide linker. The fusion protein comprises two biologically active molecules and a peptide linker linking the two active molecules. The structural formula of the fusion protein is expressed as K1-L-K2 or K2-L-K1, wherein K1 is the first biologically active molecule, L is the above-mentioned peptide linker, and K2 is the second biologically active molecule. The components of the fusion protein are sequentially linked from the N-terminus to C-terminus. Further, the active molecules may be selected from protein or protein domain, polypeptide, antibody or antibody fragment, preferably protein or protein domain, antibody or an antibody fragment.

Illustratively, the active molecule K1 of the fusion protein comprises protein or protein domain having biological function, polypeptide (e.g., especially soluble or membrane signal molecule), cytokine, growth factor, hormone, costimulatory molecule, enzyme, receptor, protein or polypeptide having ligand function for the receptor. The active molecule K2 is serum protein or protein domain that prolongs the circulation half-life, for example, human serum albumin (HSA), transferrin (TF), antibody/immunoglobulin Fc fragment, and so on.

Illustratively, the active molecule K1 of the fusion protein comprises toxin, enzyme, cytokine, membrane protein, or immunomodulatory cytokine. The active molecule K2 comprises antibody or antibody fragment. K1 and K2 are linked via the peptide linker to form an antibody fusion protein. For example, K2 is an antibody Fv fragment (VL or VH), and for another example, K2 is a single chain antibody (scFv).

Further, the biologically active molecule K1 comprises but is not limited to adenosine A1 receptor, angiotensin converting enzyme ACE, activin family, ADAM family, ALK family, α-1-antitrypsin, programmed cell death associated protein family, nerve growth factor and receptor family, bone morphogenetic protein BMP and receptor family, complement factor, calcitonin, cancer associated antigen, cathepsin family, CCL chemokine and receptor family, CD superfamily, CFTR, CXCL chemokine and receptor family, EGF, epidermal growth factor EGF and receptor family, coagulation factor IIa, factor VII, factor VIII, factor IX, ferritin, fibroblast growth factor FGF and receptor family, follicle stimulating hormone, FZD family, HGF, glucagon, cardiac myosin, growth hormone, Ig, IgA receptor, IgE, insulin-like growth factor IGF and binding protein family, interleukin IL superfamily and its receptor superfamily, interferon INF family, iNOS, integrin family, kallikrein family, laminin, L-selectin, luteinizing hormone, MMP family, mucin family, cadherin superfamily, platelet-derived growth factor PDGF and receptor family, parathyroid hormone, serum albumin, T-cell-related receptor superfamily, TGF-α, transforming growth factor TGF-β superfamily, thyroid stimulating hormone, parathyroid stimulating hormone, tumor necrosis factor TNF superfamily and its receptor TNFRSF superfamily, urokinase, WNT signaling pathway family, thymosin α1, thymosin β4, VEGF, vascular endothelial growth factor VEGF and its receptor family.

In the preferred embodiments of the present invention, the active molecule K1 is human coagulation factor VII (FVII), human coagulation factor VIII (FVIII), GLP-1 analogue Exendin-4 (Ex4), human interleukin 7 (IL-7), or human growth hormone (hGH). The peptide linker L of the fusion protein is as shown in SEQ ID no: 2, 3, 4, 5, 6 or 7. The active molecule K2 is selected from the Fc fragments of human immunoglobulins IgG, IgM, and IgA. More preferably, the Fc fragments are derived from human IgG$_1$, IgG$_2$, IgG$_3$ or IgG$_4$. Furthermore, the Fc fragments may be wild-types or variants. The Fc variants contain at least one amino acid modification in the wild-type human immunoglobulin Fc domain. The variants have reduced effector functions (ADCC or CDC effect) and/or an enhanced binding affinity for the neonatal receptor FcRn. Further, in the preferred embodiments of the present invention, the Fc variants are preferably selected from the following groups: (i) vFcγ1: human IgG$_1$ hinge, CH2, and CH3 regions containing Leu234Val, Leu235Ala and Pro331Ser mutations (the amino acid sequence is as shown in SEQ ID no: 8); (ii) vFcγ2-1: human IgG$_2$ hinge, CH2, and CH3 regions containing Pro331Ser mutation (the amino acid sequence is as shown in SEQ ID no: 9); (iii) vFcγ2-2: human IgG$_2$ hinge, CH2, and CH3 regions containing Thr250Gln and Met428Leu mutations (the amino acid sequence is as shown in SEQ ID no: 10); (iv) vFcγ2-3: human IgG$_2$ hinge, CH2, and CH3 regions containing Pro331Ser, Thr250Gln and Met428Leu mutations (the amino acid sequence is as shown in SEQ ID no: 11); (v) vFcγ4: human IgG$_4$ hinge, CH2, and CH3 regions containing Ser228Pro and Leu235Ala mutations (the amino acid sequence is as shown in SEQ ID no: 12).

More preferably, in one embodiment of the present invention, the FVII-Fc fusion protein comprises, sequentially from the N- to C-terminus, FVII (having the amino acid sequence as shown in SEQ ID no: 13), the peptide linker (having the amino acid sequence as shown in SEQ ID no: 2), and human IgG Fc (having the amino acid sequence as shown in SEQ ID no: 11).

More preferably, in one embodiment of the present invention, the FVIII-Fc fusion protein comprises, sequentially from the N- to C-terminus, FVIII (having the amino acid sequence as shown in SEQ ID no: 14), the peptide linker (having the amino acid sequence as shown in SEQ ID no: 2), and human IgG Fc (having the amino acid sequence as shown in SEQ ID no: 11).

More preferably, in one embodiment of the present invention, the Exendin-4-Fc fusion protein comprises, sequentially from the N- to C-terminus, Exendin-4 (having the amino acid sequence as shown in SEQ ID no: 15). the peptide linker (having the amino acid sequence as shown in SEQ ID no: 2, 3, 5 or 7), and human IgG Fc (having the amino acid sequence as shown in SEQ ID no: 11).

More preferably, in one embodiment of the invention, the IL-7-Fc fusion protein, sequentially from the N- to C-terminus, comprises IL-7 (having the amino acid sequence as shown in SEQ ID no: 16), the peptide linker (having the amino acid sequence as shown in SEQ ID no: 2), and human IgG Fc (having the amino acid sequence as shown in SEQ ID no: 11).

More preferably, in one embodiment of the present invention, the hGH-Fc fusion protein comprises, sequentially from the N- to C-terminus, hGH (having the amino acid sequence as shown in SEQ ID no: 17), the peptide linker (having the amino acid sequence as shown in SEQ ID no: 2), and human IgG Fc (having the amino acid sequence as shown in SEQ ID no: 11).

In other preferred embodiments of the invention, the active molecule K1 of the fusion protein is the antibody heavy chain variable region (VH), and K2 is the antibody light chain variable region (VL). K1 and K2 are linked by the peptide linker to form a single chain antibody (scFv).

In some preferred embodiments of the invention, the active molecule K1 of the fusion protein comprises a first antibody or antibody fragment, and the active molecule K2 comprises a second antibody or antibody fragment. K1 and K2 are linked by the peptide linker to form a bispecific antibody.

Preferably, in one embodiment of the present invention, K1 is a full-length double-chain anti-CD20 antibody, K2 is a single chain anti-CD3 antibody, and K1 and K2 are linked by the peptide linker to form a bispecific antibody. More preferably, the heavy chain of the anti-CD20 double-chain antibody contained in the bispecific antibody has an amino acid sequence as shown in SEQ ID no: 18 and the corresponding light chain has an amino acid sequence as shown in SEQ ID no: 19. The anti-CD3 single chain antibody contained in the bispecific antibody has an amino acid sequence as shown in SEQ ID no: 20. The peptide linker has an amino acid sequence as shown in SEQ ID no: 4 or 6. The heavy chain of the anti-CD20 double-chain antibody is linked to the anti-CD3 single chain antibody by the peptide linker.

Yet another aspect of the present invention also provides a method for preparing a fusion protein having the structural formula expressed as: K1-L-K2 or K2-L-K1, wherein K1 is the first biologically active molecule, L is the peptide linker, and K2 is a second biologically active molecule. The components that make up the fusion protein are sequentially linked from the N- to the C-terminus. The active molecules may be selected from the groups including protein or protein domain, polypeptide, antibody or antibody fragment, preferably protein or protein domain, antibody or antibody fragment. The preparation method includes the step of allowing K1 and K2 to be linked by L. In the preferred embodiments of the present invention, the method includes the following steps:

(a) Ligate the DNA sequences encoding the first active molecule K1 and the second active molecule K2 through the DNA sequence of the peptide linker L to form a fusion gene.
(b) Introduce the fusion gene obtained in step (a) into a eukaryotic or prokaryotic expression host.
(c) Culture the high yield expression host screened and obtained in step (b) to express the fusion protein.
(d) Harvest the fermentation broth of step (c) and isolate and purify the fusion protein.

Illustratively, the peptide linkers are used to link the active proteins/polypeptides to serum proteins with long circulation half-lives, such as antibody/immunoglobulin Fc fragments, human serum albumin (HSA), transferrin (TF), etc. In one preferred embodiment of the present invention, the preparation method of the FVII-Fc fusion protein includes the step of linking the active molecule FVII and human IgG Fc by the peptide linker (SEQ ID no: 2). In one preferred embodiment of the present invention, the preparation method of the FVIII-Fc fusion protein includes the step of linking the active molecule FVIII and human IgG Fc by the peptide linker (SEQ ID no: 2). In another preferred embodiment of the present invention, the preparation method of the Exendin 4-Fc fusion protein includes the step of linking the active molecule Exendin-4 and human IgG Fc by the peptide linker (SEQ ID no: 2, 3, 5 or 7). In another preferred embodiment of the present invention, the preparation method of the IL-7-Fc fusion protein includes the step of linking the active molecule IL-7 and human IgG Fc by the peptide linker (SEQ ID no: 2). In another preferred embodiment of the present invention, the preparation method of the hGH-Fc fusion protein includes the step of linking the active molecule hGH and human IgG Fc by the peptide linker (SEQ ID no: 2).

Illustratively, the peptide linkers are used in the construction of bispecific antibodies. In the preferred embodiment of the present invention, the preparation method of the bispecific antibody of anti-CD3XCD20 includes the step of linking the double-chain anti-CD20 antibody and the single chain anti-CD3 antibody by the peptide linker (SEQ ID NO: 4 or 6).

In this present invention, technical novelties can be summarized as follows:
1. In the present invention, part of the peptide linker, CTP, contains multiple O-glycosyl side chains. It is capable of forming a relatively stable and rigid three-dimensional structure and thus more effectively separate the two partners of the fusion protein and eliminate the steric hindrance between them. In the construction of a series of fusion proteins composed of the active proteins and the Fc fragment, for example, the FVII-Fc fusion protein, the introduction of the rigid CTP unit into the peptide linker ensures that the N-terminally fused active protein does not affect the binding site of the Fc variant to FcRn, thus having no effect on the circulation half-life of the fusion protein. In addition, the protein A binding site of Fc is important for the purification step, and the introduction of the rigid CTP unit ensures that the N-terminally fused active protein will not "block" the protein A binding site. On the other hand, the introduction of the rigid CTP unit makes the 25 kD size of the Fc fragment not interfere with the folding of the N-terminally fused active protein, which prevents the decline or loss of the biological activity/function of the active protein. Many embodiments of the present invention indicate that the introduction of the rigid CTP unit makes the biological activity of the fusion proteins significantly improved. This can be explained as follows. The rigid CTP polypeptide possesses multiple glycosyl side chains. Compared with irregular coil of a flexible peptide linker such as $(GGGGS)_n$ (SEQ ID NO: 38), CTP can form a stable three-dimensional conformation, which effectively increases the distance between the two fusion partners of the fusion protein. The spatial separation facilitates independent folding of the active protein and the Fc segment to form correct three-dimensional conformations, such that the active protein and the Fc segment would have no mutual impact on the biological activity of each other. This reduces the possibility of the decline or loss of the activity of the active protein due to misfolding and conformational alteration. Thus the biological activity of the fusion protein is increased.

2. The peptide linkers of the present invention have a wide range of applicability and portability. With a combination of rigid and flexible units, the peptide linkers are conferred with a conformation between completely rigid and fully flexible, and the specific rigidity or flexibility of the polypeptide varies depending on the ratio and arrangement order of the two sequences. As sequences are designed with different combinations of ratio and arrangement order of rigid and flexible units, the rigidity of the peptide linker can be finely regulated to meet different requirements in the construction of the fusion proteins.

3. CTP contains glycosylation sites. Highly sialylated and negatively charged CTP can resist the kidney to its clearance and further prolongs the half-life of the fusion protein. CTP can improve pharmacokinetic parameters, such as reducing the clearance rate, reducing the apparent distribution of volume, increasing $AUC_{(0-t)}$, such that the bioavailability of the fusion protein increases. It is expected that the clinical dose will be reduced.

4. The glycosyl side chains of CTP has protective effect, which can reduce the sensitivity of the peptide linker to proteases. The fusion protein is not easy to be degraded in the linking region.

Term Definitions

"Antibody fragment": refers to an antigen-binding fragment of an antibody or antibody analogue, which typically comprises at least a portion of the antigen-binding region or variable region of the parental antibody, for example, one or more CDRs.

The "Fc" region: includes two heavy chain fragments, each of which comprises the CH2 and CH3 domains of an antibody. The two heavy chain fragments are held together by two or more interchain disulfide bonds and the inter-CH3 domain hydrophobic interactions.

The "Fv" region comprises the variable regions from both the heavy and light chains, but lacks constant regions.

"Single chain Fv antibody" (or scFv antibody): refers to an antibody comprising the VH and VL domains of an antibody, wherein these domains are present in a single polypeptide chain. In general, the Fv polypeptide additionally contains a polypeptide linker between the VH and VL domains that allows scFv to form the desired structure for antigen binding.

"Bispecific antibody": refers to an antibody that comprises two Fv domains or scFv units such that the resulting antibody recognizes two different antigenic determinants.

"Antibody fusion protein": refers to a product obtained by fusing an antibody fragment with another bioactive protein using genetic engineering techniques. Owing to many different fused proteins, the antibody fusion proteins have a variety of biological functions.

For example, an Fv-containing antibody fusion protein. As the Fab or Fv fragment is linked with certain toxins, enzymes, or cytokines, the biologically active molecules can be targeted to specific sites of the targeted cell, forming the so-called "biological missile.

For example, chimeric receptors. As the scFv antibody is fused with certain cell membrane protein molecules, the fusion proteins, known as chimeric receptors, can be expressed on the cell surface, giving the cells the capability to bind to a specific antigen.

For example, an Fc-containing antibody fusion protein. The antibody IgG Fc region is fused with the biologically active molecule to form an Fc fusion protein. The Fc fusion protein not only exerts the biological function of the active molecule but also inherits similar properties of the antibody, including prolonged plasma half-life and a series of effector functions specific to the Fc region. For example, on the one hand, the Fc region plays an important role in the eradication of pathogens. The Fc-mediated effector functions of IgG are carried out by two mechanisms: (1) After the Fc regions of IgG molecules bind to the cell surface Fc receptors (FcγRs), pathogens are broken down by phagocytosis or lysis or by killer cells through an antibody-dependent cell-mediated cytotoxicity (ADCC) pathway. (2) After the Fc regions of IgG molecules bind to C1q molecules of the first complement C1 complexes, the complement-dependent cytotoxicity (CDC) pathway is triggered, such that pathogens are lysed. On the other hand, the antibody Fc region bind to the FcRn receptor to prevent the antibody from entering into lysosome to be degraded. The fusion proteins containing the Fc region are endocytosed and protected by FcRn. These fusion proteins are not to be degraded, but again enter into the circulatory system, thereby increasing the in vivo half-lives of these fusion proteins. Moreover, FcRn shows activity in adult epithelial tissues, and it is expressed in epithelial cells of the intestine, pulmonary trachea, nasal cavity, vagina, colon, and rectum. The fusion proteins containing the Fc region can effectively shuttle the epithelial barrier through FcRn-mediated cell transduction.

"hCG-β carboxy terminal peptide (CTP)": is a short peptide derived from the carboxyl terminus of human chorionic gonadotropin (hCG) beta subunit. Four kinds of reproduction-related polypeptide hormones, follicle stimulating hormone (FSH), luteinizing hormone (LH), thyroid stimulating hormone (TSH), and human chorionic gonadotropin (hCG) comprise the same alpha subunit and respective specific beta subunits. Compared with the other three hormones, hCG has a significantly prolonged half-life, which is mainly due to the specific carboxyl terminal peptide (CTP) on its β-subunit. CTP has 37 amino acid residues, which possesses four O-glycosylation sites terminating with a sialic acid residue. Highly sialylated, negatively charged CTP can resist to the clearance by the kidney, thereby prolonging the in vivo half-life of a protein (Fares F A et al., 1992, Proc Natl Acad Sci USA, 89: 4304-4308).

EXAMPLES

Figure 1:
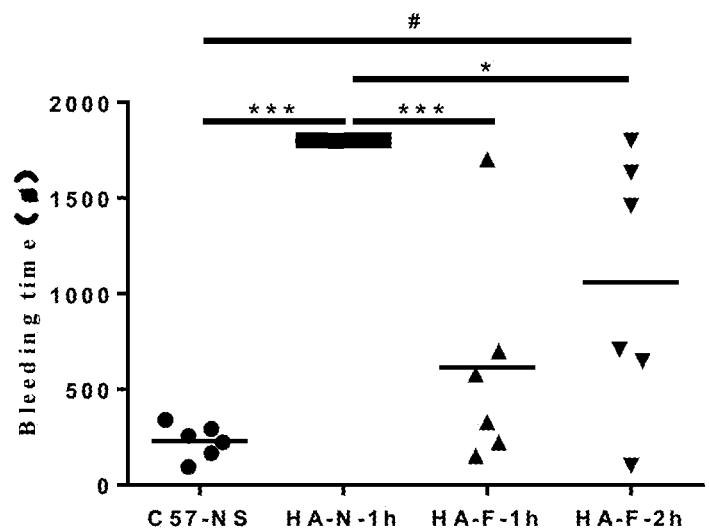
FIG. 1. Comparison of the bleeding times of HA mice administered with FP-A1 and NovoSeven® for 1 h and 2 h. Compared with the HA-N-1h group, *P<0.05, ***P<0.01; compared with the C57-NS group, #P<0.05, ###P<0.01.

Example 1. Peptide Linkers Used to Construct Fusion Proteins

The present inventors constructed a series of fusion proteins K1-L-K2 containing peptide linkers. The composition of each fusion protein was shown in Table 1. The DNA sequences encoding the first active molecule K1 and the second active molecule K2 were ligated by the DNA sequence of the peptide linker L to constitute a fusion gene. Preferably, the codons of the DNA sequences were optimized for expression in CHO cells. Preferably, the sequences were generated by chemical synthesis. Two restriction sites, SpeI and EcoRI, were added at the 5' and 3' ends of the synthesized fragment, respectively, to facilitate insertion of the fusion gene obtained above into the specific site of an expression vector. After verified by sequencing, the fusion gene was digested with the corresponding restriction endonucleases and inserted into the corresponding cleavage sites of the expression plasmid PXY1A1, obtained by modifying PCDNA3.1 as a template. The expression plasmid containing the gene of the fusion protein was thus obtained. The PXY1A1 plasmid contained, but was not limited to, the following important expression elements: 1) human cytomegalovirus immediate early promoter and highly exogenous expression enhancer needed by mammalian cells; 2) double screening markers with kanamycin resistance in bacteria and G418 resistance in mammalian cells; 3) murine dihydrofolate reductase (DHFR) gene expression cassette. When the host cell type was DHFR gene deficient, methotrexate (MTX) could co-amplify the fusion gene and the DHFR gene (U.S. Pat. No. 4,399,216). The expression plasmid of the fusion protein was transfected into a mammalian host cell line. The preferred host cell line was DHFR enzyme-deficient CHO cells in order to achieve stable and high levels of expression (U.S. Pat. No. 4,818,679). After two days of transfection, the medium was replaced with a screening medium containing 0.6 mg/mL G418. Cells were seeded in the 96-well plate at a certain concentration (5000-10000 viable cells/well) for 10-14 days until large discrete cell clones appeared. The transfectants resistant to the selecting antibiotic were screened by the ELISA assay. Subclones with high level expression of the fusion protein were isolated by limiting dilution and use of the 96-well culture plate. For a fusion protein already validated as a good one by multiple means, it was appropriate to amplify the DHFR gene by MTX drug inhibition to achieve higher level of expression. In the growth medium containing increasing concentration of MTX, the transfected fusion protein gene was co-amplified with the DHFR gene. The highly expressed monoclonal cell strains obtained were cultured under fed-batch conditions in shake flasks or a 5-liter fermentor. The fusion protein was purified by protein A affinity chromatography and other ion exchange chromatography.

The inventors constructed a series of fusion proteins containing the present invention's peptide linkers with flexible and rigid units, and also constructed a variety of fusion proteins containing the peptide linkers with only flexible units of different lengths for comparison. For example, FVII-Fc fusion protein (FP-A1 containing CTP; FP-A2 and FP-A3 without CTP), FVIII-Fc fusion protein (FP-B1 containing CTP; FP-B2 and FP-B3 without CTP); Fc-fusion protein of Exendin-4 and its analogue (FP-C1, FP-C2, FP-C3, FP-C4 containing CTP; FP-C5 without CTP), IL7-Fc fusion protein (FP-D1 containing CTP; FP-D2 without CTP), hGH-Fc fusion protein (FP-E1 containing CTP; FP-E2 without CTP). In addition, the inventors also developed anti-CD20XCD3 bispecific antibodies (FP-F1 and FP-F2 containing CTP). The composition of each fusion protein was shown in Table 1, and the amino acid sequence of each fusion protein was shown in the sequence listings section.

TABLE 1

The compositions of various fusion proteins from N- to C-terminus

| Code for fusion protein | K1 | L | K2 |
|---|---|---|---|
| FP-A1 | FVII | F2-R1 | Fc (vFcγ$_{2-3}$) |
| FP-A2 | FVII | F1 | Fc (vFcγ$_{2-3}$) |
| FP-A3 | FVII | F3 | Fc (vFcγ$_{2-3}$) |
| FP-B1 | FVIII | F2-R1 | Fc (vFcγ$_{2-3}$) |
| FP-B2 | FVIII | F1 | Fc (vFcγ$_{2-3}$) |
| FP-B3 | FVIII | F3 | Fc (vFcγ$_{2-3}$) |
| FP-C1 | Exendin-4 | F2-R1 | Fc (vFcγ$_{2-3}$) |
| FP-C2 | Exendin-4 | F1-R2 | Fc (vFcγ$_{2-3}$) |
| FP-C3 | Exendin-4 | F5-R5 | Fc (vFcγ$_{2-3}$) |
| FP-C4 | Exendin-4 | F6-R4R4R4 | Fe (vFcγ$_{2-3}$) |
| FP-C5 | Exendin-4 | F1 | Fc (vFcγ$_{2-3}$) |
| FP-D1 | IL-7 | F2-R1 | Fc (vFcγ$_{2-3}$) |
| FP-D2 | IL-7 | F1 | Fc (vFcγ$_{2-3}$) |
| FP-E1 | hGH | F2-R1 | Fc (vFcγ$_{2-3}$) |
| FP-E2 | hGH | F1 | Fc (vFcγ$_{2-3}$) |
| FP-F1 | Anti-CD20 mAb | F4-R1 | Anti-CD3 ScFv |
| FP-F2 | Anti-CD20 mAb | F4-R3R3 | Anti-CD3 ScFv |

Example 2. Preparation of Coagulation Factor FVII-Fc Fusion Proteins and Determination of Biological Activity and In Vivo Active Half-Life 2.1 Preparation and Identification of Coagulation Factor FVII-Fc Fusion Proteins The stably expressing CHO cell strains of FP-A1, FP-A2 and FP-A3 obtained in Example 1 were cultured in shake flasks under fed-batch conditions for 10-14 days. The fusion proteins were purified by four steps of column chromatography: protein A affinity chromatography, multidimensional chromatography, anion exchange chromatography, and molecular sieve chromatography. The fusion proteins were then self-activated with incubation in a solution. The SDS-PAGE electrophoresis showed the following results. Under reducing conditions, the single-chained molecule of non-activated FP-A2 showed two obvious bands in the vicinity of 70-85 kDa and 40 kDa, indicating that protein degradation occurred and the fraction of the degraded fragments was about 20-30%. Under non-reducing conditions, the non-activated FP-A2 migrated to about 130 kDa together with another band of >200 kDa, indicating that some of the fusion proteins aggregated. Under reducing conditions, the single-chained molecule of non-activated FP-A3 was close to 100 kDa and there were no contaminant bands. Under non-reducing conditions, most of the non-activated FP-A3 proteins migrated to >200 kDa, indicating that FP-A3 was in the form of aggregates. Under reducing conditions, the single-chained molecule of non-activated FP-A1 was of 100-110 kDa and there were no obvious contaminant bands. Under non-reducing conditions, the non-activated FP-A1 migrated to 150 kDa. Under reducing conditions, the activated FP-A1 showed two clear bands, 74.3 kDa HC-L-CTP-Fc and about 24.0 kDa LC, respectively, and no other contaminant bands. Under non-reducing conditions, the activated FP-A1 migrated to 150 kDa, indicating that the fusion protein FP-A1 did not degrade significantly, did not form aggregates remarkably, and had higher thermodynamic stability and stronger ability of anti-proteolytic hydrolysis. This example demonstrated that the peptide linkers containing the rigid CTP unit increased the stability of the fusion proteins, which were less susceptible to degradation, and reduced the formation of aggregates.

2.2 Direct Determination of the Biological Activity of Fusion Proteins by the Clotting Assay The determination of FVIIa biological activity by the clotting assay was achieved by correcting FVIIa-deficient plasma to prolong the clotting time. The kit (STAGO, Cat. No. 00743) was used for the assay. The assay was first to mix diluted human freeze-dried normal plasma of known FVII activity (Unicalibrator, Cat. No. 00625) with FVII-deficient plasma, measure the prothrombin time (PT), and establish a standard curve. The plasma for the FVII activity to be measured was diluted and then mixed with FVII-deficient plasma for PT measurement. The FVIIa activity of the test sample could be determined from the logarithmic equation between the percentage of activity C (%) and PT time t (s) fitted by the standard curve. The FVIIa activity was expressed as the percentage (%) of that of normal plasma. The corresponding relation between the percentage of activity of the standards (%) provided by the kit and the international unit (IU) of enzyme activity was 100%=1 IU, according to which the specific activity of FVII in the test sample could be calculated in units of IU/mg. The results showed that under optimum experimental conditions, the highest activities of FP-A1, FP-A2 and FP-A3 were about 20000 IU/mg, 4000 IU/mg and 7000 IU/mg, respectively. The experimental results showed that the type and length of the peptide linkers had a great effect on the activity and stability of FVII-Fc. The in vitro bioactivity of the fusion protein FP-A1 containing the peptide linker with the rigid unit was much higher than those of the fusion proteins FP-A2 and FP-A3 without rigid units. The results also showed that if only the length of the flexible peptide was extended, the activity of the fusion protein could not be improved effectively. The steric hindrance between the fused partners comprised the formation of the correct conformation of the fusion proteins, such that the stability of the fusion proteins decreased and the proteins were easy to form aggregates. This example demonstrated that the peptide linker containing a rigid CTP unit reduced the steric hindrance of the Fc domain and increased the activity and stability of the fusion protein.

2.3 Determination of In Vivo Bleeding Inhibition of FVII-Fc Fusion Proteins

The hemostatic effect of FVII-Fc fusion proteins was assessed by using hemophilia mice, which were the tail vein transection (TVT) bleeding model of homozygous hemophilia A mice with knockout of the FVIII factor gene (HA, Shanghai Research Center of the Southern Model Organisms). Male HA mice, 16-20 weeks old, were adaptively fed for one week and randomly divided into 3 groups, 6 mice per group. Two groups were given 300,000 IU/kg of FP-A1 and the other group was given 300,000 IU/kg of NovoSeven® (Novo Nordisk). Meantime, wild-type male C57BL/6J mice, 16-20 weeks old (Shanghai Research Center of the Southern Model Organisms), were used as the normal control group (n=6), and given an equal volume of physiological saline through tail vein injection. The two groups of HA mice given FP-A1 were subjected to tail-cutting tests at 1 h and 2 h after administration, respectively, and the HA mice given Novo-Seven® were subjected to tail-cutting tests at 1 h after administration. The C57BL/6J normal control group (C57-NS group) was subjected to tail-cutting tests at 2 h after administration. All data were expressed as mean±standard error (±SEM). The t-test analysis was used to compare between the experimental groups. The analysis software was Graphpad Prism 5.0. $P<0.05$ was considered statistically significant.

As shown in FIG. 1, after administration of NovoSeven® for 1 h, the bleeding time of the mice was 30 min, indicating that it had no hemostatic effect (HA-N-1h group). In contrast, after administration of FP-A1 for 1 h (HA-F-1h group) and 2 h (HA-F-2h group), FP-A1 was still effective in hemostasis, and the bleeding times were significantly shorter than that of the NovoSeven® group ($P<0.05$). This indicated that FP-A1 had a significantly longer active half-life compared with NovoSeven®.

2.4 Determination of In Vivo Active Half-Life of FVII-Fc Fusion Protein

In this study, we investigated the active half-life of FP-A1 in the warfarin-induced coagulation disorder rat model. According to the method reported in the literature (Joe Salas et al., 2015, Thrombosis Research, 135:970-976 or Gerhard Dickneite et al., 2007, Thrombosis Research, 119:643-651), SD rats (8-12 weeks age and 220 g body weight, Beijing Vital River Laboratory Animal Technology Co., Ltd.) were randomly divided into two groups, eight rats per group. After intragastric administration of warfarin (Orion Corporation, Finland, lot no. 1569755) at a dose of 2.5 mg/kg for 24 h, the rats were given intravenous administration of 10,000 IU/kg of FP-A1 or NovoSeven® (Novo Nordisk), respectively. Blood was collected after administration for the FP-A1 group at 0.05 h, 0.5 h, 1 h, 2 h, 3 h, 5 h, 8 h, 12 h, respectively, and for the NovoSeven® group at 0.05 h, 0.5 h, 1 h, 2 h, 3 h, 5 h, respectively. With sodium citrate at a final concentration of 0.013 M as an anticoagulant, blood samples were centrifuged at 3000 rpm for 10 min to obtain the supernatant. The activity was determined by the method in section 2.2 and the active half-life was calculated.

Figure 2:
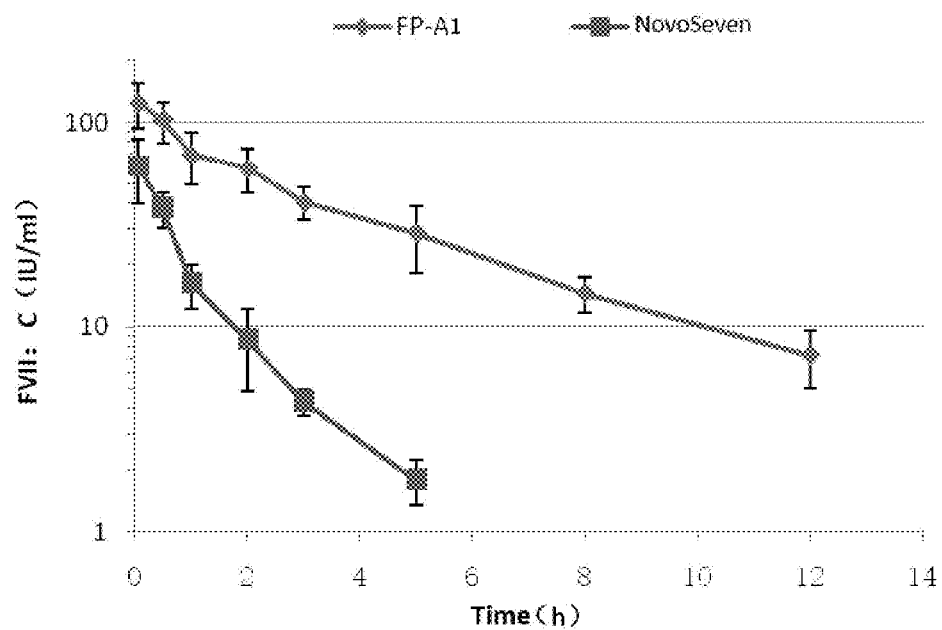
FIG. 2. The active half-lives of FP-A1 and NovoSeven® in rats administered with warfarin.

As shown in FIG. 2, the active half-life of FP-A1 was calculated to be 3.03±0.35 h, and that of NovoSeven® was 1.01±0.16 h. Compared with NovoSeven® with equal activity, FP-A1 prolonged the active half-life in rats by about 3-fold. The plasma coagulation activity was about 40% at 3 h after single injection of FP-A1, while the coagulation activity of NovoSeven® decreased to 3% after 3 h. At 12 h after administration, the plasma coagulation activity of FP-A1 remained 7% or more.

The results in sections 2.3 and 2.4 showed that the fusion protein of the present invention, containing the peptide linker with the flexible and rigid CTP units, had a significantly prolonged active half-life, indicating that the peptide linker eliminated the blocking effect of the active protein FVII on the binding site of Fc for its receptor FcRn. The results also demonstrated that owing to the introduction of the peptide linker of the present invention, FVII formed the correct three-dimensional conformation, maintained high biological activity, and was not affected by the steric hindrance of the C-terminally fused Fc.

Example 3. Production of Coagulation Factor FVIII-Fc Fusion Proteins and Determination of Biological Activity 3.1 Production and Identification of Coagulation Factor FVIII-Fc Fusion Proteins The stably expressing CHO cell strains for FP-B1, FP-B2 and FP-B3 obtained in Example 1 were cultured for 7 to 12 days under fed-batch or semi-continuous culture conditions. The supernatant was harvested immediately for purification by protein A and/or VIII-select (GE) affinity chromatography. Under optimum culture conditions, the FP-B2 supernatant was passed through protein A and VIII-select (GE) two-step affinity chromatography columns, and the elute still contained multiple components. Under reducing conditions, the SDS-PAGE electrophoresis showed a main band of 180 kDa and multiple fragments of 40-100 kDa. Under non-reducing conditions, most of the purified proteins migrated to >300 kDa. This indicated that FP-B2 products were mostly in the form of aggregates, unstable and easy to be degradated. Under the same culture conditions, the supernatant of FP-B1 was purified by protein A and VIII-select (GE) two-step affinity chromatography. Under reducing conditions, three clear bands appeared on the gel, which were single chain FVIII-Fc (190 kDa), light chain-Fc (105 kDa) and heavy chain (90 kDa), and there were no contaminant bands. Under non-reducing conditions, purified proteins FP-B1 and FP-B3 migrated to >200 kDa, while most of FP-B3 proteins stayed in the stacking gel, indicating that FP-B3 was also present in the form of aggregates.

It was reported that the lipid binding region of FVIII (2303-2332) was critical to its function, and that very small conformational changes in the region led to protein aggregation and loss of activity (Gilbert et al., 1993, Biochemistry, 32:9577-9585). The results of the present invention indicated that the peptide linker containing the rigid CTP unit could eliminate the steric hindrance of the C-terminal Fc on the FVIII lipid-binding region, such that the FVIII spatial conformation was almost unaffected. Thus, the protein aggregation was reduced, the protein stability was increased, and the bioactivity of the FVIII-Fc fusion protein was greatly improved.

3.2 Direct Determination of the Biological Activity of the FVIII-Fc Fusion Proteins by the Clotting Assay The determination of the FVIII biological activity by the clotting assay was achieved by correcting FVIII-deficient plasma to prolong the clotting time. A factor VIII (FVIII) assay kit (the clotting method), STA®-Deficient FVIII (STAGO, Cat. No. 00725), was used. The method was first to determine the activated partial thromboplastin time (APTT) of normal human freeze-dried plasma (Unicalibrator, Cat No. 00625) of known coagulation factor VIII activity. The test instrument was a STAGO START® hemostasis analyzer. A standard curve was established. Then the FVIII-Fc fusion protein was mixed with the factor VIII-deficient plasma, and APTT values were determined. The logarithmic equation between the percentage of activity C (%) and APTT time t (s) fitted by the standard curve could be used to determine the activity of the test sample FVIII-Fc. The activity was expressed as the percentage (%) of that of normal plasma. The corresponding relation between the percentage of activity of the standards provided by the assay kit and the international unit (IU) of enzyme activity was 100%=1 IU, according to which the specific activity of FVIII in the test sample could be calculated, expressed as IU/mg. The results showed that under optimum experimental conditions, the highest activities of FP-B1, FP-B2 and FP-B3 were 10000 IU/mg, 150 IU/mg and 1300 IU/mg, respectively. Considering that most of the FP-B2 protein molecules were in the form of inactive aggregates or degraded fragments, the actual specific activities of FP-B2 and FP-B3 that were in active forms were not necessarily very different. This indicated that extending the length of the flexible peptide linker had a limited effect on improving the activity of the fusion protein FVIII-Fc. FP-B1 and FP-B2 showed a significant difference between the specific activities, which indicated that the rigid CTP unit in the peptide linker could reduce the steric hindrance of the Fc domain and improved the activity of the FVIII-Fc fusion protein.

Example 4. Production of Exendin-4-Fc Fusion Proteins and Determination of Biological Activity and In Vivo Active Half-Life 4.1 In Vitro Biological Activity The stably expressing CHO cell strains of FP-C1, FP-C2, FP-C3, FP-C4 and FP-C5 obtained in Example 1 were cultured in shake flasks under fed-batch conditions for 12-14 days. The fusion proteins were purified by Protein A affinity chromatography, and used for activity analysis. The purity of the fusion proteins was above 95%, and the molecular sizes were as expected. For the in vitro activity assay, referred to the literature (Zlokarnik G et al, 1998, Science, 279:84-88). The method was briefly described as follows. First, the human GLP-1R expression plasmid and the expression plasmid PGL-4.29 (Luc2P/CRE/Hygro) (Promega) carrying the CRE-Luc reporter gene were co-transfected into CHO-K1 cells. Then stable cell strains co-expressing both the plasmids were obtained after screening by antibiotic pressure. For the in vitro activity assay, 16000 cells per well in 200 μL medium were inoculated into the 96-well cell culture plate. The cells were cultured in DMEM medium containing 10% FBS for 16-24 h, until they grew to cover more than 90% of the bottom of the wells. The fusion proteins FP-C1, FP-C2, FP-C3, FP-C4 and FP-C5 were diluted with DMEM medium containing 10% FBS, and 10 μL was added to each well of the 96-well culture plate. The concentration gradients were set to 0.010, 0.020, 0.039, 0.078, 0.156, 0.313, 0.625, 1.25, and 2.5 nM. Meantime an equal concentration gradient of duraglutide (Eli Lilly, Cat. No. 9301897) was set as positive control. After the cells were incubated at 37° C., 5% $CO_2$ for 5-6 h, the supernatant was aspirated. The cells were washed slowly by adding 300 μL of PBS/well, then PBS was aspirated. 40 μL of lysis buffer was added and shaken for 15 min, and then 40 μL of luciferase substrate (Genomeditech (Shanghai) Co., Cat. No. GM-040501B, luciferase reporter gene detection kit) was added to each well. After 2 min reaction time, the fluorescence was measured at a wavelength of 560 nm using a multi-function microplate reader (SpectraMax M5 system, Molecular Device). A dose response curve was plotted based on the fluorescence values. The $EC_{50}$ value was calculated. The results were shown in Table 2. The $EC_{50}$ values of FP-C1, FP-C2, FP-C3, FP-C4 and FP-C5 were 0.03086 nM, 0.03156 nM, 0.03684 nM, 0.04012 nM and 0.03586 nM, respectively, and that of duraglutide was 0.02987 nM. The in vitro biological activities of CTP-containing FP-C1, FP-C2, FP-C3, FP-C4 and CTP-free FP-C5 were comparable. As the inventors understood, for a simple small molecule polypeptide such as Exendin-4, the steric hindrance of Fc to Exendin-4 was small, the effect of CTP that eliminated the steric hindrance and increased the activity of the fusion protein was not evident.

TABLE 2

Comparison of in vitro activity $EC_{50}$ values of fusion proteins

| Fusion protein | FP-C1 | FP-C2 | FP-C3 | FP-C4 | FP-C5 | Duraglutide |
|---|---|---|---|---|---|---|
| $EC_{50}$ (nM) | 0.03086 | 0.03156 | 0.03684 | 0.04012 | 0.03586 | 0.02987 |

4.2 Blood Glucose Concentration Changes in db/db Diabetic Mice Given Single Injection of FP-C1 or FP-C5

Female diabetic db/db mice (Shanghai SLAC Laboratory Animals Co., Ltd.), 8 weeks old, weighing 42±2 g, were randomly divided into 3 groups, with 6 mice per each group. The drug-testing groups were injected subcutaneously with FP-C1 or FP-C5 at a dose of 3 mg/kg. The positive group was injected with 3 mg/kg of duraglutide (Eli Lilly, Cat. No. 9301897). The control group was injected with an equal volume of PBS buffer (10 mL/kg). Blood samples were collected from the tail vein at 0 h (before administration), 1 h, 2 h, 4 h, 6 h, 24 h, 48 h, 72 h, 96 h, 120 h, 144 h, 168 h, 192 h, 216 h (after administration). The blood glucose meter was used to measure random blood glucose (RBG) concentrations for recording the data. The blood glucose data were expressed as mean±standard deviation (mean±SD) and analyzed using the SPSS 18.0 statistical software package.

Figure 3:
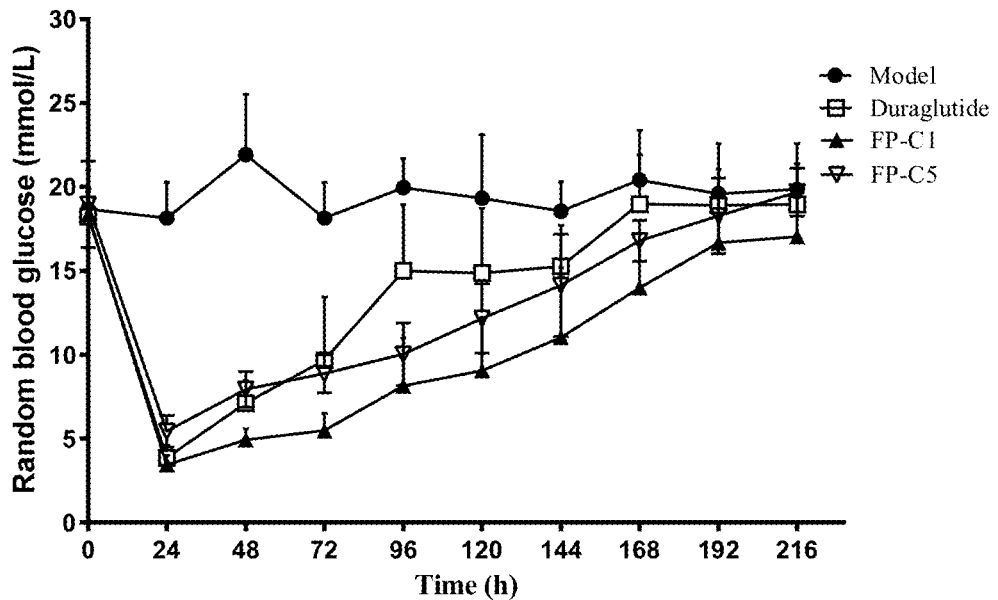
FIG. 3. The curves of the RBG value changes in 0-216 h in db/db diabetic mice given single injection of FP-C1 and FP-C5.

At the same dose, FP-C1, FP-C5 and the positive control drug duraglutide all had significant hypoglycemic effects. FIG. 3 showed the curves of 9-day mouse RBG values after administration. The hypoglycemic effect of duraglutide could only be maintained until day 4 ($P>0.05$). At 120 h after administration, the blood glucose level had no statistical difference compared with that of the control group. In contrast, FP-C1 could lower the blood glucose level of the mice for 168 h after administration, that was, the blood glucose level of the mice on the 7th day after administration was still statistically different from that of the control group ($P<0.05$). FP-C5 could maintain the hypoglycemic effect for 144 h after administration, that was, on the 6th day after administration the blood glucose level of the mice was still statistically different from that of the control group. Thus, compared with FP-C5, FP-C1 had a longer-term hypoglycemic effect in the diabetic mouse model. This indicated that the rigid CTP unit in the peptide linkers could further extend the in vivo functional half-life of Exendin-4.

4.3 Pharmacokinetic Characteristics of Exendin-4-Fc Fusion Proteins in Rats

Male SPF SD rats (Shanghai SIPPR-BK Laboratory Animal Co. Ltd.), 4 per group, were given a single subcutaneous injection of 0.5 mg/kg FP-C1 or FP-C5 after one week of pre-feeding. Blood was taken at 0 h (before administration), 2 h, 8 h, 24 h, 32 h, 48 h, 56 h, 72 h, 96 h, 120 h, 144 h (after administration), respectively, about 0.3 mL each time. The blood collection time points were marked as $T_0$, $T_2$, $T_8$, $T_{24}$, $T_{32}$, $T_{48}$, $T_{56}$, $T_{72}$, $T_{96}$, $T_{120}$, and $T_{144}$, respectively. The blood was allowed to settle down. Then the serum was separated by centrifugation at 5000 rpm for 10 min, and the serum samples were stored at −70° C. and analyzed. The concentrations of fusion proteins were determined by the double-antibody sandwich ELISA assay. Used for coating was self-made or commercially available anti-Exendin-4 or GLP-1 N-terminal monoclonal antibody (e.g., Santa Cruz, Cat. No. SC-65389), and used as the detection antibody was self-made or commercially available horseradish peroxidase-labeled mouse anti-human-IgG-Fc monoclonal antibody (e.g., Sino Biological Inc., Cat. No. 10702-MM01E-50). The data were input into the analysis software PKSolver, and pharmacokinetic parameters such as $T_{1/2}$, $C_{max}$ and $AUC_{(0-t)}$ of the tested drug were obtained.

As shown in Table 3, the circulation half-life $T_{1/2}$ of 0.5 mg/kg of FP-C5 in rats was 14.9±1.29 h, whereas the $T_{1/2}$ of 0.5 mg/kg of FP-C1 in rats was 21.4±2.51 h. The maximum plasma concentration $C_{max}$ of FP-C1 was significantly higher than that of FP-C5. In addition, by comparing $AUC_{0-t}$ (t=2 h, 5 h, 8 h, 24 h, 28 h, 32 h or 48 h) at different blood collection time points, we could see that at the same dose, the drug exposure of FP-C1 was significantly higher than that of FP-C5, that was, the absolute bioavailability of FP-C1 in rats was higher than that of CTP-free FP-C5. It was expected that the clinical dose of FP-C1 would also decrease.

TABLE 3

Pharmacokinetic parameters of single subcutaneous injection of 0.5 mg/kg FP-C1 or FP-C5 in male SD rats

|  | $T_{1/2}$ (h) | $T_{max}$ (h) | $C_{max}$ (ng/mL) | AUC(0~∞)ng/mL · h |
|---|---|---|---|---|
| FP-C1 | 21.4 ± 2.51 | 24 | 700.908 | 35260.92 ± 2041.20 |
| FP-C5 | 14.9 ± 1.29 | 48 | 369.167 | 12535.06 ± 909.42 |

4.4 Random Blood Glucose and HbA1c Changes in db/db Diabetes Mouse after 10 Weeks of FP-C1 Treatment.

Female SPF-db/db mice (Shanghai slack experimental animal company), 8 weeks old, were fed for 1 week and divided into 4 groups with 6 in each group based on the RBG: model group, Low FP-C1 group (0.75 mg/kg), middle FP-C1 group (1.5 mg/kg), high FP-C1 group (3 mg/kg). Corresponding concentrations of the drug has been hypodermic injected, and PBS has been injected in the model group with 10 ml/kg. Mice in each group were treated with drug once a week for 10 weeks and subjected to blood glucose meter to measure the RBG in each time point. Data were recorded. Blood sampling points were 0 d (before drug treatment), 7 d, 14 d, 21 d, 28 d, 35 d, 42 d, 49 d, 56 d, 63 d and 70 d after drug treatment. At the 70$^{th}$ day, mice in each group were blood sampled from the eyes after a 14 h fast and samples were subjected to the HbA1c kit and the corresponding H700 specific protein analyzer to detect the level of HbA1c. Results were shown as the percentage of HbA1c in the total blood proteins.

Date were presented as mean±SD which was generated by SPSS18.0. Differences between the means in the normal distribution were analysed by single factor variance. Homogeneity of variance was examined by Dunnett t-test and heterogeneity of variance was examined by Dunnett's T3 test. Abnormal distribution was examined by non-parametric test. P<0.05 showed significant statically difference.

From the variations of blood glucose of the mice in Table 4, mice in high, middle, low FP-C1 groups showed decreased levels of blood glucose compared with the model group, and their decreased blood glucose levels showed dose-dependent. These data indicated that FP-C1 effectively, continuously maintained the blood glucose level in db/db diabetes mice. Moreover, the hypoglycemic effect of the first administration and the last administration was similar, indicating that no drug resistance reaction occurred, which might lead to the anti-FP-C1 tolerance.

Figure 4:
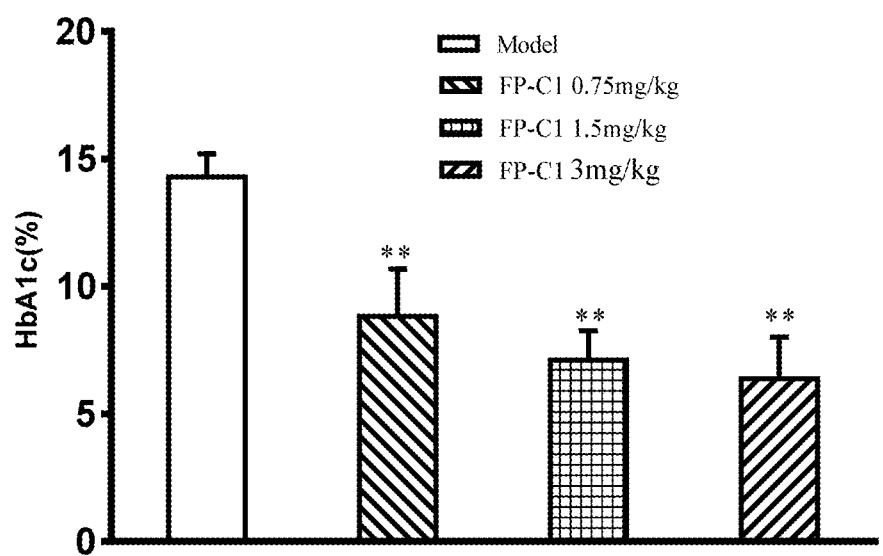
FIG. 4. The effect of different doses of FP-C1 on HbA1c in db/db diabetes mice. Comparison of the FP-C1 group with the model group, *P<0.05, **P<0.01.

HbA1c was the product that glucose was bound to hemoglobin in the red blood cell, and showed proportional relationship with the glucose level in the blood. Because the red blood cell has a circulation half-life of 120 days, HbA1c represented the total glucose level in the blood in the 4-12 weeks before blood sampling, making up the shortcoming that the fasting blood sugar only reflected the transient blood sugar. So, HbA1c was the most critical indicator of monitoring blood glucose level and also one of the important factors to be considered in the clinical trial. The result of HbA1c in this example could reliably, stably reflect the blood glucose level 2-3 months before blood sampling. The amount of HbA1c in the mice with 10 weeks' drug treatment was shown in FIG. 4. The amount of HbA1c in the FP-C1 groups decreased significantly compared with that of the model group (P<0.01), showing dose-dependent. The amount of HbA1c in the high FP-C1 group decreased remarkably (6.38±1.63) but was still higher than that in the normal C57BL/6J mice (2.5%-3.5%), indicating that 3 mg/kg of FP-C1 would not lead to the occurrence of long-term hypoglycemia. In conclusion, our results showed that FP-C1 chronically, effectively, stably controlled the blood sugar level in the mice without increasing the risk of long-term hypoglycemia. It was consistent with the trend of blood glucose changes in Table 4.

TABLE 4

The effect of FP-C1 on random blood glucose in db/db mice

| Group | RBG (mmol/L) | | | | |
|---|---|---|---|---|---|
|  | 7 d | 14 d | 21 d | 28 d | 35 d |
| Model | 19.5 ± 3.53 | 23.84 ± 3.28 | 21.9 ± 4.16 | 24.08 ± 2.18 | 21.92 ± 2.39 |
| Low-dose | 16.04 ± 1.98 | 18.5 ± 1.38** | 17.36 ± 3.87 | 19.58 ± 3.5* | 16.54 ± 3.41 |
| Middle-dose | 15.19 ± 2.65* | 17.34 ± 2.27* | 15.42 ± 3.6* | 17.82 ± 1.54** | 14.02 ± 3.42* |
| High-dose | 11.92 ± 1.95** | 15.26 ± 3.15** | 12.54 ± 3.97** | 15.36 ± 3.18** | 11.78 ± 4.2** |

| Group | RBG (mmol/L) | | | | |
|---|---|---|---|---|---|
|  | 42 d | 49 d | 56 d | 63 d | 70 d |
| Model | 23.58 ± 3.51 | 23.66 ± 1.9 | 21.2 ± 4.72 | 23 ± 04.09 | 25.04 ± 5.24 |
| Low-dose | 16.02 ± 2.07** | 19.26 ± 2.17* | 13.92 ± 3.53* | 16.88 ± 3.92* | 17.46 ± 3.0* |
| Middle-dose | 14.3 ± 1.49** | 16.2 ± 2.86** | 12.6 ± 3.53** | 14.5 ± 4.37** | 15.14 ± 2.81** |
| High-dose | 12.12 ± 3.95** | 15.38 ± 2.43** | 9.46 ± 3.45** | 11.52 ± 3.93** | 11.76 ± 5.35** |

Note:
Compared with model group, *P < 0.05; **P < 0.01.

4.5 Pharmacodynamic Study of Single Injection of FP-C1 in STZ Induced Diabetes Mice Male SPF mice (Shanghai slack experimental animal company) with the weight of 25±2 g were divided into the diabetes group and the control group based on their weights. Mice were fed for one week and subjected to a 18 h fast. The weights of the mice were recorded. The diabetes group was treated with 150 mg/kg 1% STZ, pH=4.4 by intraperitoneal injection. While the control group was treated the same volume of citric acid sodium citrate buffer. The RBG of the mice was recorded 10 days after the injection. The mice with RBG≥16.7 h were selected as the diabetes mice. 32 STZ-induced mice were selected and divided into 4 groups with 8 in each group to observe the hypoglycemic effect of test drugs on STZ-induced diabetic mice. 3 mg/kg FP-C1 and 3 mg/kg dulaglutide were injected subcutaneously, respectively. An equal volume (10 mL/kg) of PBS buffer was administered to the diabetes model group and the control group, respectively. The mice in each group are blood sampled from tail vein at 0 h (before drug treatment), 1 h, 2 h, 4 h, 6 h, 24 h, 48 h, 72 h, 96 h, 120 h, 144 h, 168 h, 192 h, 216 h (after drug treatment). Samples were subjected to the blood sugar meter to measure the RBG. Data were presented as mean±sd and analyzed by SPSS18.0. Differences between the means in the normal distribution were analysed by single factor variance. The homogeneity of variance was examined by LSD test and the heterogeneity of variance was examined by Dunnett's T3 test. Abnormal distribution was examined by non-parametric test. $P<0.05$ indicated significant statistical difference.

Figure 5:
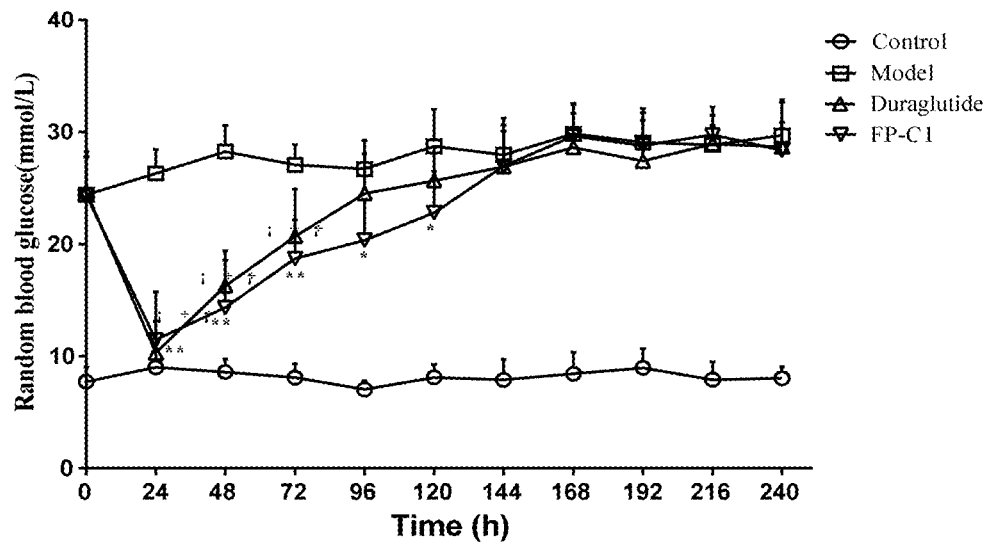
FIG. 5. RBG value changes of STZ-induced diabetes mice with single injection of FP-C1 during 0-240 h. Comparison of the FP-C1 group with the model group, *P<0.05, **P<0.01; Comparison of the Duraglutide group with the model group, ΔP<0.05, ΔP<0.01.

FIG. 5 showed the curves of the blood glucose concentration changes during 0-240 h in STZ-induced mice after single injection of FP-C1, FP-C1 decreased RBG effectively. The blood glucose level in the FP-C1 group decreased to the minimum at the 24 h after the FP-C1 treatment. Then it went back slowly but still showed significant difference compared with that of the model group ($P<0.05$).

4.6 Study on the Effect of FP-C1 on Weight Loss in Obese Mice Induced by High Fat Diet 1. Model Establishment and Drug Treatment 24 C57BL/6J male mice (Shanghai Slack Experimental Animal Company, SCXK(HU): 2012-0002) with 7 weeks old. Feeding environment: temperature 22-25° C., relative humidity 45-65%. Lighting time 12 h/d. The C57BL/6J mice were fed for one week and then divided into 3 groups based on the weights: NFD group, HFD group, FP-C1 group (HFD+FP-C1 0.3 mg/kg). The HFD group and the FP-C1 group were fed with high-fat diet (D12492 high fat diet, Research Dowts CO. USA). The NFD group was fed with normal fat diet. The FP-C1 group was injected with 0.3 mg/kg FP-C1 every 6 days, while the NFD group and the HFD group were injected with 10 ml/kg PBS buffer. The mice in each group had a 16 h fast after 96 days and the weights and blood sugar levels were recorded. Blood was sampled and subjected to 400 g centrifugation for 15 min to obtain the serum. After blood was taken, the mice were sacrificed by cervical dislocation, and the length from nose to anus (body length) was measured to calculate the Lee's index. The fat tissue around the epididymis was separated and weighed. The same tissue was stocked in 10% formaldehyde solution for further experiment.

2. Detection of Parameters 2.1 Body Weight and Obesity Degree

Mice were weighed every 6 days to draw the curve of body weight and the increased amount was recorded. Increased amount=body weight at the final weighing−body weight before grouping. Lee's index was used to describe the obesity degree.

2.2 Fat Mass and its Fraction

Analytical balance was used to weigh the fat tissue around the epididymis. Fat mass fraction was calculated as fat mass fraction=weight of fat tissue (mg)/fasting weight (g).

2.3 Oral Glucose Tolerant Test

After 84 days of experimentation, mice in each group were fasted for 16 hours (17:00 am-9:00 pm). The blood glucose meter was used to measure the fasting blood glucose (FBG). The body weights were recorded. 2 g/kg glucose solution was fed, and the blood sugar levels were detected after 30 min, 60 min, 90 min and 120 min of the gavage. The sugar tolerance curve was drawn and iAUC was calculated based on the modified curve.

2.4 Serum Test

Automatic biochemical analyzer and corresponding kit were used to detect the concentration of TG and TC in the serum.

2.5 Parameters of Insulin and Islet Tolerance

ELISA was used to detect the concentration of insulin in the serum to calculate the insulin tolerance.

2.6 Pathological Examination of the Fat Tissue

Fat tissue around the epididymis was subjected to HE dyeing to visualize the fat tissue cell.

3. Statistics and Analysis

Data were presented as means±SD and analyzed by SPSS18.0. Differences between the means in the Normal distribution were analysed by single factor variance. Homogeneity of variance was examined by LSD test and heterogeneity of variance was examined by Dunnett's T3 test. Abnormal distribution was examined by non-parametric test. $P<0.05$ showed significant statistical difference.

Figure 6:
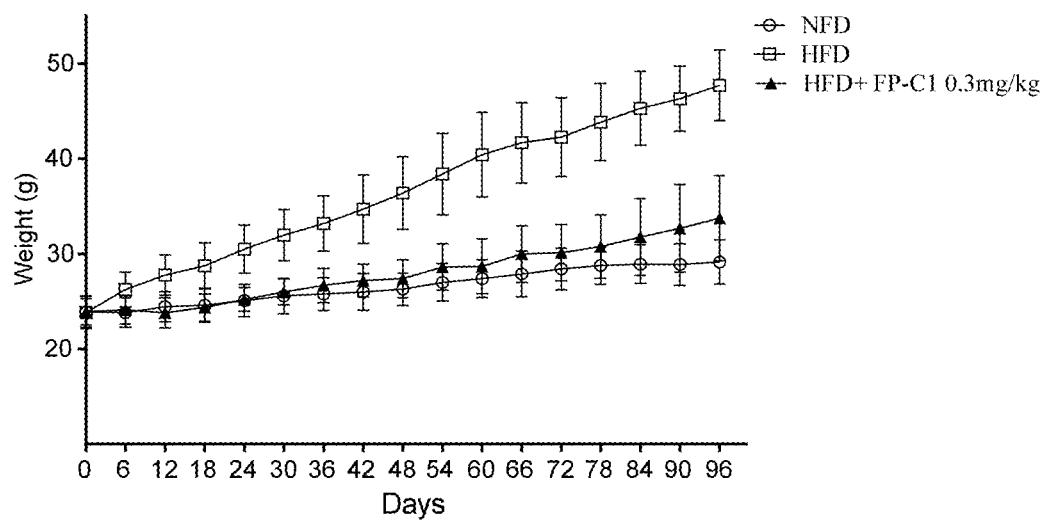
FIG. 6. The effect of FP-C1 on the body weight of mice fed with high fat diet.

4. Results 4.1 Effect of FP-C1 on Body Weight and Obesity Degree of Mice Fed with High-Fat Diet Compared with those in the NFD group, the body weight, the increased body weight and Lee's index all significantly increased ($P<0.01$). FP-C1 effectively decreased the body weight, the increased body weight, and Lee's index ($P<0.01$). Data were shown in Table 5 and FIG. 6.

TABLE 5

The effect of FP-C1 on body weight and Lee's index in high fat diet induced obese mice

| Group | Final body weight (g) | Body weight gain (g) | Lee's index |
|---|---|---|---|
| NFD | 29.14 ± 2.31 | 5.24 ± 1.09 | 322.7 ± 11.03 |
| HFD | 47.7 ± 3.74## | 23.9 ± 2.57## | 348.78 ± 10.21## |
| FP-C1 | 33.74 ± 4.5** | 9.81 ± 4.24** | 327.67 ± 10.28** |

Note:
Compared with normal group, #$P < 0.05$, ##$P < 0.01$;
Compared with HFD group, *$P < 0.05$, **$P < 0.01$ 4.2 Effect of FP-C1 on the Fat Mass and Mass Fraction Around the Epididymis As shown in Table 6, compared with the NFD group, the mice in HFD group showed more fat mass and mass fraction around the epididymis ($P<0.01$). Compared with the HFD group, mice in FP-C1 group showed decreased fat mass and mass fraction around the epididymis ($P<0.05$).

TABLE 6

The effect of FP-C1 on Epididymal fat and its index

| Group | Epididymal fat (g) | Epididymal fat index (mg/g) |
|---|---|---|
| NFD | 0.68 ± 0.12 | 25.29 ± 3.83 |
| HFD | 2.91 ± 0.45## | 64.1 ± 10.85## |
| FP-C1 | 1.54 ± 0.69* | 46.09 ± 14.77* |

Note:
Compared with normal group, #$P < 0.05$, ##$P < 0.01$;
Compared with HFD group, *$P < 0.05$, **$P < 0.01$ 4.3 Effect of FP-C1 on the Concentrations of TG and TC in the Serum Compared with NFD group, the concentrations of TG and TC in the serum in the HFD group increased significantly ($P<0.01$). Compared with HFD group, the concentrations of TG and TC in the serum in the FP-C1 group decreased significantly ($P<0.01$). Data shows in Table 7.

TABLE 7

The effect of FP-C1 on serum TG and
TC in high fat diet induced obese mice

| Group | TG (mmol · L$^{-1}$) | TC (mmol · L$^{-1}$) |
|---|---|---|
| NFD | 1.81 ± 0.31 | 4.34 ± 0.25 |
| HFD | 2.93 ± 0.33## | 7.77 ± 0.85## |
| FP-C1 | 1.98 ± 0.38** | 5.78 ± 0.85** |

Note:
Compared with normal group, #P < 0.05, ##P < 0.01;
Compared with HFD group, *P < 0.05, **P < 0.01

4.4 Effect of FP-C1 on Glucose Tolerance in Mice Fed with High Fat Diet

Figure 7:
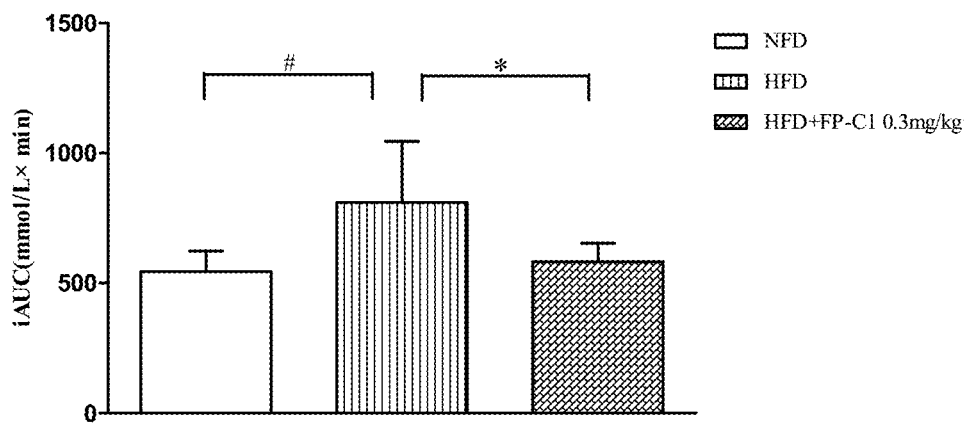
FIG. 7. The effect of FP-C1 on glucose tolerance in mice fed with high fat diet (mean±SD, n=8). Compared with the normal group, #P<0.05, ##P<0.01; compared with the high fat group, *P<0.05, **P<0.01.

As shown in FIG. 7, iAUC in the HFD group is significantly higher than that in NFD group (P<0.05). Compared with the HFD group, iAUC in the FP-C1 group decreases significantly (P<0.05).

Figure 8:
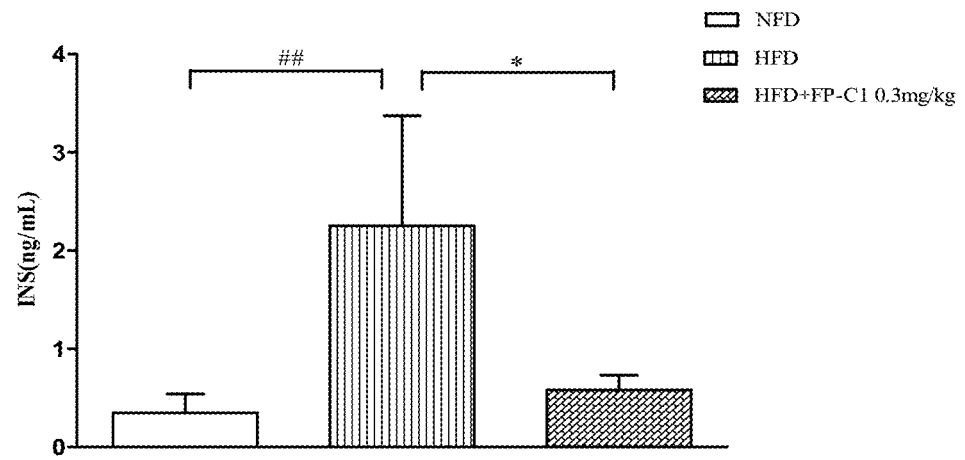
FIG. 8. The effect of FP-C1 on the serum insulin concentration of mice fed with high fat diet (means±SD, n=8). Compared with the normal group, #P<0.05, ##P<0.01; compared with the high fat group, *P<0.05, **P<0.01.
Figure 9:
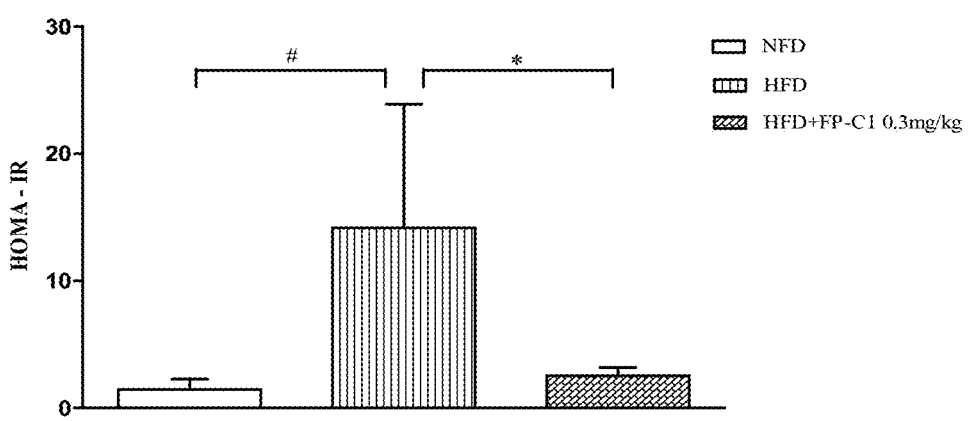
FIG. 9. The effect of FP-C1 on the insulin resistance index of mice fed with high fat diet (mean±SD, n=8). Compared with the normal group, #P<0.05, ##P<0.01; compared with the high fat group, *P<0.05, **P<0.01.

4.5 Effect of FP-C1 on Serum Insulin Concentration and Insulin Resistance Index in Mice Fed with High Fat Diet Compared with those in the NFD group, the insulin concentration and the insulin resistance index in the HFD group increased significantly, which meant that the mice obviously have already obtained insulin tolerance, and they would secreted more insulin to produce hyperinsulinemia. Compared with those in the HFD group, FP-C1 decreased the INS concentration (P<0.05) and improved the HOMA-IR (P<0.05) significantly. Results were shown in FIG. 8 and FIG. 9.

4.6 Pathomorphological Examination

Figure 10:
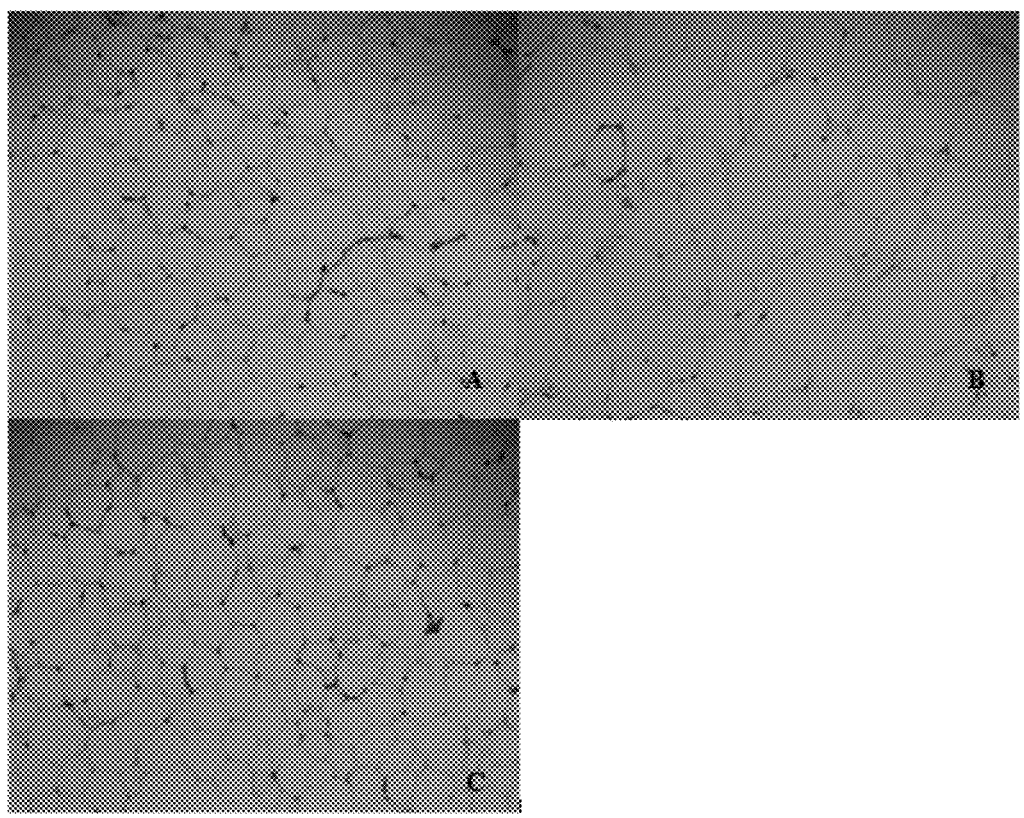
FIG. 10. The effect of FP-C1 on the cross-sectional area of fat cells in mice fed with high fat diet. A: normal group. B: high fat diet group. C: FP-C1 group.

HE dyeing showed that the cross-sectional area of fat cells around the epididymis in the HFD group increased significantly compared with the NFD group. Compared with that in the HFD group, the cross-sectional area of fat cells around the epididymis in the FP-C1 group decreased significantly. Results were shown in FIG. 10.

In conclusion, FP-C1 could control the body weight of the HFD induced fat mice and has the anti-obesity effect.

Figure 11:
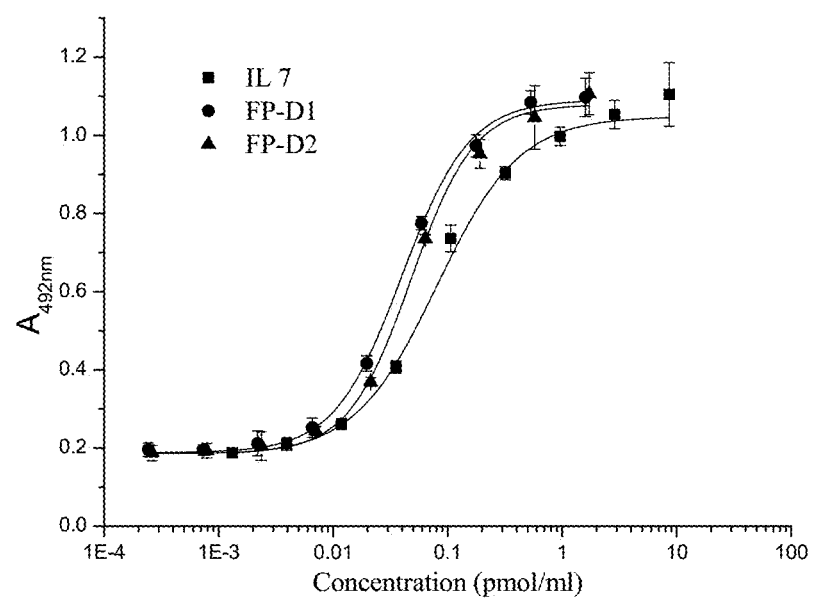
FIG. 11. The ability of IL7-Fc fusion proteins FP-D1 and FP-D2 to stimulate mouse mononuclear cells to proliferate.

Example 5. Production of IL-7-Fc Fusion Proteins and Determination of Biological Activity and In Vivo Active Half-Life 5.1 In Vitro Biological Activity The stably expressing CHO cell strains of FP-D1 and FP-D2 obtained in Example 1 were cultured in shake flasks under fed batch conditions for 12-14 days. The fusion proteins were purified by Protein A affinity chromatography. The purity of both the fusion proteins was above 95%, and the molecular sizes were also as expected. The fusion proteins were then used for activity analysis. The in vitro biological activity analysis of IL-7 and its fusion proteins was performed as follows. The mouse spleen-derived mononuclear cells were activated by concanavalin A (ConA), and then 100 μL of the cells were seeded into each well of a 96-well plate, followed by addition of a series of concentration gradient of FP-D1 or FP-D2. The cells were cultured at 37° C., 5% $CO_2$ for 72 h, and after addition of 20 μL of MTT reagent, were continued to culture for 4 h. The medium was aspirated and 100 μL of dimethyl sulfoxide (DMSO) was added to each well. The absorbance at 492 nm was used to determine the proliferation of the cells. Three replicates were performed for each concentration gradient, and each replicate was measured twice. Recombinant IL-7 (hIL-7, Sino Biological Inc.) was used as positive control and the medium was used as negative control. FIG. 11 showed the ability of hIL-7, FP-D1 and FP-D2 fusion proteins to stimulate the proliferation of mouse mononuclear cells. Based on the dose response curves plotted, the half maximal effective concentration values ($EC_{50}$) of the FP-D1 and FP-D2 fusion proteins were 0.039 and 0.048 nM, respectively. The recombinant fusion proteins exhibited better in vitro bioactivity than hIL-7 that E. coli expressed ($EC_{50}$ value of 0.08 nM in terms of molarity).

5.2 Determination of Pharmacokinetic Parameters of IL-7-Fc Fusion Proteins

Male SPF SD rats (Shanghai SIPPR-BK Laboratory Animal Co. Ltd.), 3 per group, were given a single intravenous (iv) or subcutaneous (sc) injection of 2 mg/kg FP-D1 or FP-D2 after one week of pre-feeding. The changes of blood drug concentration with time were investigated. At 0 h, 3 h, 6 h, 24 h, 48 h, 72 h, 96 h, 120 h, 126 h, 144 h, and 172 h after injection, blood was collected, about 0.3 mL each time. The blood was allowed to settle down. Then the serum was separated by centrifugation at 5000 rpm for 10 min and taken for assay. The fusion protein concentration at each time point was determined by an ELISA method specific for human IL-7. The data were analyzed by the PKSolver software, and pharmacokinetic parameters such as $T_{1/2}$ and $AUC_{(0-t)}$ were calculated. The results were shown in Table 8.

TABLE 8

Pharmacokinetic parameters of fusion proteins

| Drug | $T_{1/2}$(h) iv | $T_{1/2}$(h) sc | AUC 0-inf_obs (ng/mL * h) iv | AUC 0-inf_obs (ng/mL * h) sc | Vz/F_obs ((μg)/(ng/mL)) iv | Vz/F_obs ((μg)/(ng/mL)) sc | Cl/F_obs ((μg)/(ng/mL)/h) iv | Cl/F_obs ((μg)/(ng/mL)/h) sc |
|---|---|---|---|---|---|---|---|---|
| FP-D1 | 18.760 ± 1.109 | 19.870 ± 2.287 | 24458.54 ± 8739.60 | 10310.28 ± 1364.23 | 0.526 ± 0.143 | 1.293 ± 0.173 | 0.020 ± 0.006 | 0.045 ± 0.005 |
| FP-D2 | 12.86 ± 4.32 | 13.81 ± 4.47 | 12025.16 ± 2074.52 | 4497.43 ± 571.93 | 0.79 ± 0.32 | 0.11 ± 0.01 | 0.04 ± 0.01 | 2.2 ± 0.75 |

The data showed that the elimination half-lives of FP-D2 were 12.86 h (iv) and 13.81 h (sc), respectively, which fit with linear metabolic kinetics. The elimination half-lives of FP-D1 were 18 h (iv) and 19 h (sc), respectively, slightly longer than those of FP-D2. The overall clearance rate (Cl) of FP-D1 by intravenous administration was less than that of FP-D2, indicating that after FP-D2 was modified to generate FP-D2, the in vivo clearance rate of FP-D1 was slowed down compared with that of FP-D2. In addition, we also found that due to the introduction of the CTP structure, the apparent volume of distribution of FP-D1 was reduced. This indicated that FP-D1 was less distributed in tissues and had a higher concentration in the blood, thus having a higher in vivo exposure. FP-D1 had the rigid CTP structure compared with FP-D2, which reduced the clearance, reduced the apparent volume of distribution, and increased $AUC_{(0-t)}$.

Therefore, the bioavailability of FP-D1 was higher, and the efficacy of FP-D1 might be better than that of FP-D2. It was expected that the clinical dose of FP-D1 would also decrease. Thus, FP-D1 exhibited excellent performance in terms of biological activity and pharmacokinetics. The results of this experiment indicated that the highly sialylated, negatively charged CTP in the peptide linkers could resist the clearance of the kidney, further prolong the half-lives of the fusion proteins, and increase the bioavailability of the fusion proteins.

Example 6. Production of hGH-Fc Fusion Proteins and Determination of Biological Activity and In Vivo Half-Life 6.1 Determination of In Vitro Biological Activity of Fusion Proteins by MTT Assay The stably expressing CHO cell strains of FP-E1 and FP-E2 obtained in Example 1 were cultured in shake flasks under fed-batch conditions for 12-14 days. The fusion proteins were purified by Protein A affinity chromatography. The purity of the fusion proteins was above 95%, and the molecular sizes were as expected. The fusion proteins were then used for activity analysis. In vitro hGH biological activity could be determined by measuring proliferation of Nb2 rat lymphoma cells. Since the Nb2 cells responded to the stimulation of hGH on the lactating receptors of the Nb2 cells to proliferate, the Nb2 cell proliferation assay could be used to evaluate the biological activity of growth hormone (Uchida H et al., 1999, J Mol Endocrinol, 23: 347-353).

Nb2-11 rat lymphoma cells (ATCC) were cultured in Fischer's medium containing 10% FBS. The fusion protein was diluted with serum-free medium, diluted from 1000 ng/mL to 8 gradients at 1:3 ratio, and added to a 96-well plate, 100 μL per well, with the last column using the medium as negative control. The cells growing in the log phase were washed with serum-free medium, and adjusted to a density of $3 \times 10^6$ cells/mL. 100 μL cell suspension was added to each well of the above 96-well plate. The cells were continued to culture for 48 h in a 37° C., 5% $CO_2$ incubator, and cell proliferation was measured using a CCK-8 kit (Cell Counting Kit, Cat. No. 40203ES80, Shanghai Yisheng Biotechnology Co., Ltd.). The absorbance at 450 nm was measured using a microplate reader and the OD readings were plotted against the concentrations of the fusion protein. The biological activity of the fusion protein could be determined from the resulting dose response curve.

Figure 12:
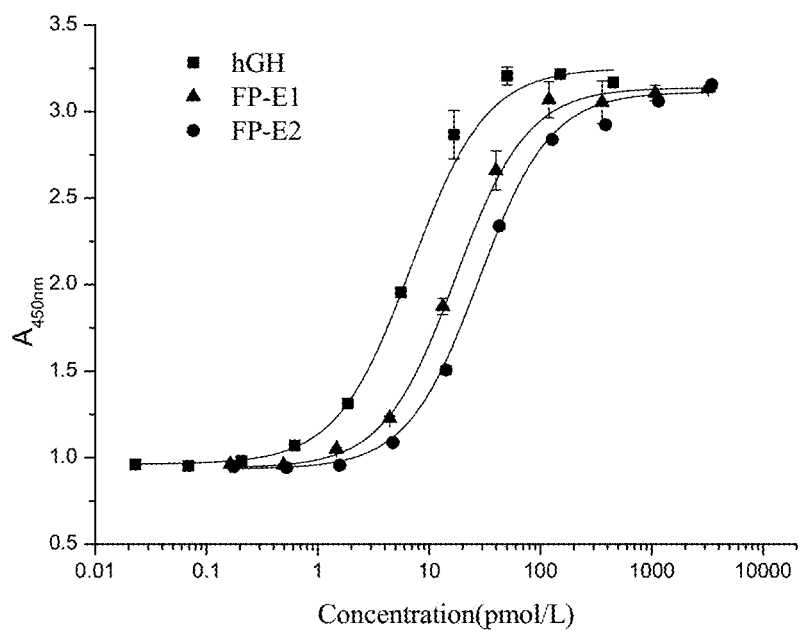
FIG. 12. The ability of hGH-Fc fusion proteins FP-E1 and FP-E2 to stimulate Nb2 cells to proliferate.

FIG. 12 showed the ability of hGH fusion proteins to stimulate the proliferation of Nb2 cells. Table 9 showed the $EC_{50}$ values for different fusion proteins. Since the amino acids at the C-terminus of growth hormone were closely related to its function, direct linking of Fc to the C-terminus of hGH might affect its biological activity. As the peptide linker was added between hGH and Fc, the activity of the hGH fusion protein was increased. As can be seen from the results, the activity of FP-E1 was nearly doubled compared with that of FP-E2. This might be due to the fact that CTP peptide did not only play its role in prolonging the half-life of the fusion protein, but also the rigid structure of CTP peptide together with a flexible peptide acted as a linker connecting Fc to the target protein. This novel peptide linker facilitated folding of the fusion protein into a stable three-dimensional structure, thus increasing the biological activity of hGH.

TABLE 9

| $EC_{50}$ values of hGH fusion proteins | | | |
|---|---|---|---|
| Fusion protein | hGH | FP-E1 | FP-E2 |
| $EC_{50}$ (pM) | 6.94 | 17.3 | 27.84 |

6.2 In Vivo Circulation Half-Life

Male SPF SD rats (Shanghai SIPPR-BK Laboratory Animal Co. Ltd.), weighing about 290 g, were divided into groups after one week of pre-feeding, with 3 in each group, and were given a single intravenous injection of 0.176 mg/kg FP-E1 or FP-E2. The changes of blood drug concentration with time were investigated. For the control group and the drug-administered group, blood was collected at 0 h, 0.5 h, 1 h, 2 h, 3 h, 4 h, 5 h, 8 h, 10 h, 24 h, 48 h, and 72 h after administration. The blood was placed at room temperature for 30 min and then centrifuged at 5000 rpm for 10 min. The serum was separated and stored at −20° C. Serum hGH levels at various time points were determined using an ELISA assay specific for hGH. The main pharmacokinetic parameters of each group were calculated by the PKSolver software. The pharmacokinetic parameters of each group were shown in Table 10.

TABLE 10

| Pharmacokinetic parameters of hGH fusion proteins | | | | | | | |
|---|---|---|---|---|---|---|---|
| Drug | $T_{1/2}$(h) | Tmax (h) | Cmax (ng/mL) | $AUC_{(0-t)}$ | $MRT_{(0-\infty)}$ (h) | Vz(μg)/(ng/mL) | Cl(μg)/(ng/mL)/h |
| FP-E1 | 2.39 ± 0.37 | 0.5 h | 4259.4396 | 16483.295 ± 4483.39 | 3.34 ± 0.43 | 0.027 ± 0.002 | 0.008 ± 0.002 |
| FP-E2 | 2.57 ± 0.04 | 0.5 h | 2414.7499 | 8987.14 ± 986.33 | 3.33 ± 0.01 | 0.054 ± 0.008 | 0.015 ± 0.002 |

Figure 13:
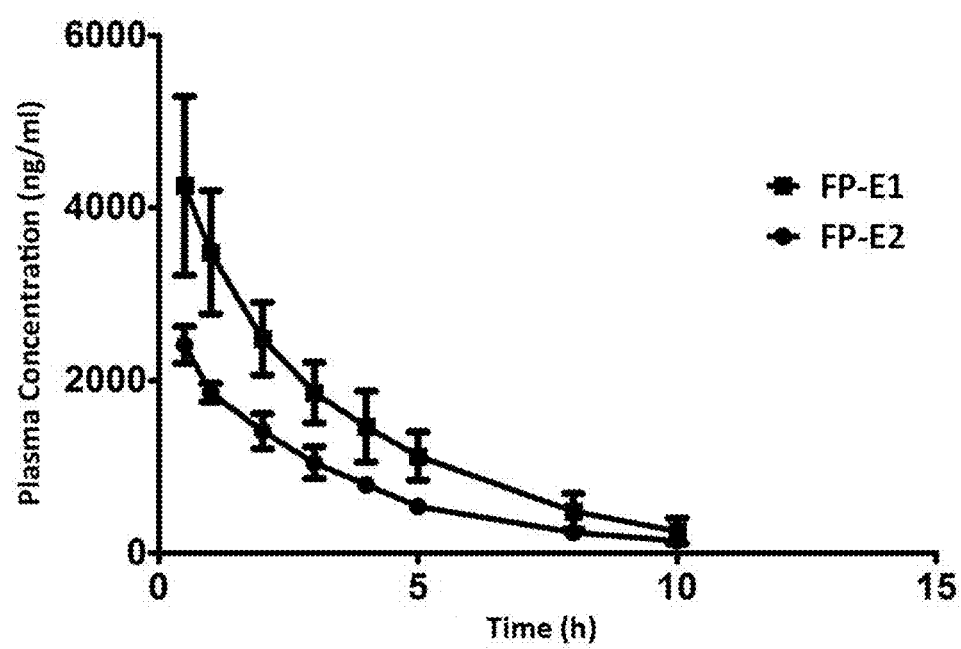
FIG. 13. The curves of blood drug concentration vs. time of hGH-Fc fusion proteins FP-E1 and FP-E2.

From the results, the in vivo half-lives of FP-E1 and FP-E2 fusion proteins were 2.6 h and 2.4 h, respectively. The half-lives were basically the same, and this could also be seen from the MRT parameters. The times that FP-E1 and FP-E2 stayed in the body were also close. According to the blood drug concentration-time curve of FIG. 13, the blood concentration of FP-E1 was always higher than that of FP-E2. It was speculated that structural changes of FP-E1 resulted in the changes in the properties of its pharmacokinetics. The total body clearance of FP-E1 was only half of that of FP-E2, indicating that the in vivo clearance of FP-E1 was relatively slow. The apparent volume of distribution of FP-E2 was twice that of FP-E1, indicating that FP-E2 was rapidly distributed into tissues after entering the body, causing its blood concentration to be lower than that of FP-E1. FP-E1 had the rigid CTP structure compared with FP-E2, which reduced the clearance, increased $AUC_{(0-t)}$, and reduced the apparent volume of distribution. This indicated that FP-E1 was less distributed in tissues and had higher concentration in the blood, resulting in higher in vivo exposure. So the structural advantage of FP-E1 was reflected not only in the superior pharmacokinetic parameters, but also in that its efficacy could be better than that of FP-E2. FP-E1 had a higher blood concentration due to the structural modifications, which meant that its bioavailability was higher. So FP-E1 was better than FP-E2, and its clinical dose could be expected to decrease. Thus, FP-E1 exhibited superior performance in terms of biological activity and pharmacokinetics.

6.3 Determination of In Vivo Biological Activity of Fusion Proteins

Male Sprague-Dawley rats (SPF grade with four weeks age and 60-80 g body weight) were provided by the Experimental Animal Center of China National Institutes for Food and Drug Control.

The pituitary gland was removed by surgery with two week's recovery period. Before administration, the qualified healthy animals were selected, whose body weight changes were less than ±10% of the preoperative weights. The pituitary gland-removed rats were randomly divided into 6 groups, 5 animals per group. Regular rhGH (trade name norditropin, Novo Nordisk A/S, activity of 3 IU/mg) was used as the positive reference drug 1 (Y1) in this experiment. PEG-rhGH (Changchun GeneScience Pharmaceuticals Co., Ltd., activity of 6 IU/mg) was used as the positive reference drug 2 (Y2). Low, median and high doses of FP-E1 were set at 5 mg/kg/14 d, 15 mg/kg/14 d, and 45 mg/kg/14 d, respectively. Based on the molecular weight and the number of molecules, the median dose of FP-E1, 15 mg/kg/14 d, was comparable to the positive reference drugs Y1 and Y2. The mode of administration was subcutaneous injection in the neck. Different doses of FP-E1 fusion protein and Y2 were administered to each rat once on the first day and the other on the eighth day. Y1 was administered once a day for 14 consecutive days.

Figure 14:
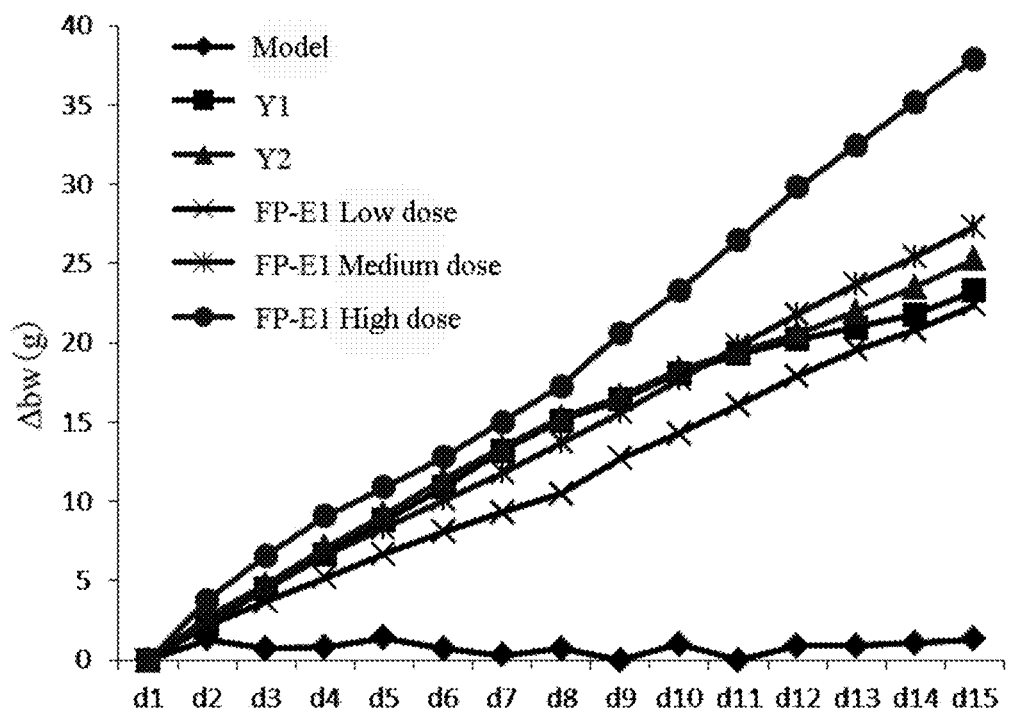
FIG. 14. The growth curves of all groups of rats administered with the hGH-Fc fusion protein FP-E1.

Each rat was weighed daily after administration. All rats were sacrificed by carbon dioxide asphyxiation on the 15th day, and weighed. The difference between the day i (di) body weight ($bw_i$) of each animal and the body weight before administration, i.e. the day 1 (d1) body weight ($bw_1$), was the increased body weight. If necessary, an autopsy could be performed at the end of the experiment. The sella region was cut, and the presence or absence of pituitary residue was examined by the naked eye. The animals with residual pituitary gland were removed. The weight gain calculation formula was: $\Delta bw = bw_i - bw_1$, wherein $\Delta bw$ was the weight gain; $bw_1$ was the d1 body weight before administration; and $bw_i$ was the day i body weight after administration. The measurement data were expressed as mean±standard deviation (M±SD), and the results were shown in Table 11. FIG. 14 showed the growth curves of all groups after administration.

TABLE 11

Body weight changes of rats before and after hGH fusion protein administration (M ± SD, n = 7)

| Group | Total dose for 2 weeks mg/kg | bw (g) before administration d1 | Δbw (g) after administration d8 | Δbw (g) after administration d15 |
|---|---|---|---|---|
| Control | 0 | 72.4 ± 6.9 | 0.7 ± 1.4 | 1.3 ± 1.7 |
| Y1 | 5.8 | 73.1 ± 5.2 | 15.1 ± 2.5 | 23.3 ± 4.4 |
| Y2 | 2.9 | 72.2 ± 6.4 | 15.3 ± 2.3 | 25.3 ± 4.3 |
| Low dose of FP-E1 | 5 | 74.3 ± 6.8 | 10.5 ± 1.3 | 22.4 ± 2.9 |
| Median dose of FP-E1 | 15 | 72.4 ± 4.8 | 13.7 ± 3.1 | 27.3 ± 6.8 |
| High dose of FP-E1 | 45 | 73.6 ± 5.9 | 17.3 ± 2.1 | 37.9 ± 3.0 |

As could be seen from the results, compared with the control group, each of the administration groups had its body weight significantly increased on the 8th day after administration, but the differences of Δbw between the administration groups were not significant. On the 15th day after administration, FP-E1 had a very significant promotive effect on the body weight gain of rats. The weight gain (Δbw) of pituitary-removed rats induced by the high dose FP-E1 was about 1.5 times those of the rhGH (Y1) and PEG-rhGH (Y2) groups. The weight gain induced by the median dose FP-E1 was slightly larger than that of the Y1 group, and was basically equal to that of the Y2 group. We found that the high dose FP-E1 group had their body weights significantly increased after the second administration, and FP-E1 showed a more significant promotive effect on weight gain than PEG-rhGH. However, within one week after the first administration, the Δbw values of the high dose FP-E1 and PEG-rhGH groups were not statistically different. Based on the analysis of the Δbw differences, it was deduced that FP-E1 should have a longer in vivo active half-life than PEG-rhGH. Thus, after repeated administration, this in vivo drug accumulation effect caused the upward trend of the growth curve of the FP-E1 group steeper after the second administration.

Example 7. Production and Biological Activity Analysis of Anti-CD3×CD20 Bispecific Antibodies 7.1 Preparation and Identification of Anti-CD3×CD20 Bispecific Antibodies The stably expressing CHO cell strains of FP-F1 and FP-F2 obtained in Example 1 were cultured in shake flasks under fed-batch conditions for 10-14 days. The bispecific antibodies were purified by Protein A affinity chromatography. The purity of both the fusion proteins was more than 95%, and the molecular sizes were as expected. The proteins were then used for activity analysis.

7.2 Determination of In Vitro Activity of Anti-CD3×CD20 Bispecific Antibodies

Figure 15:
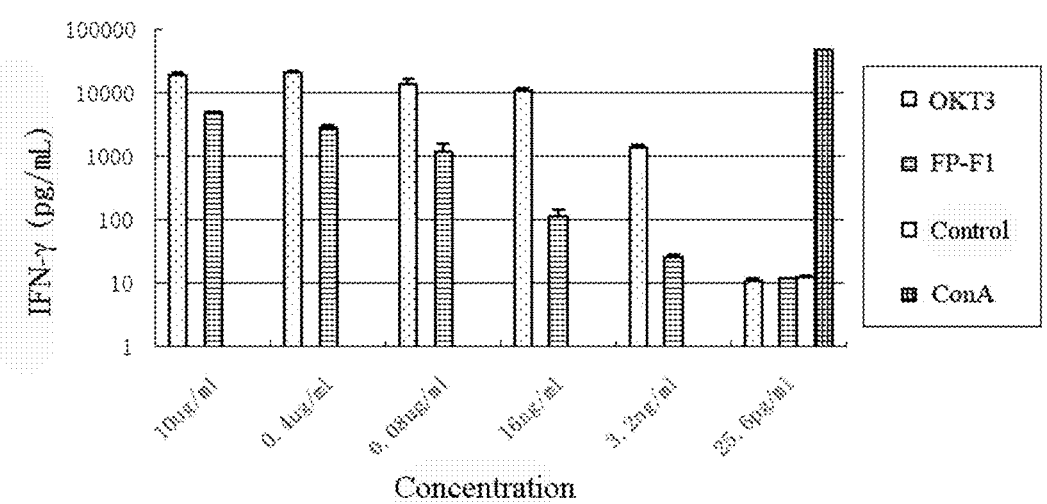
FIG. 15. The anti-CD3×CD20 bispecific antibody FP-F1 activated human PBMC cells to secret IFN-γ in a concentration-dependent manner.
Figure 16:
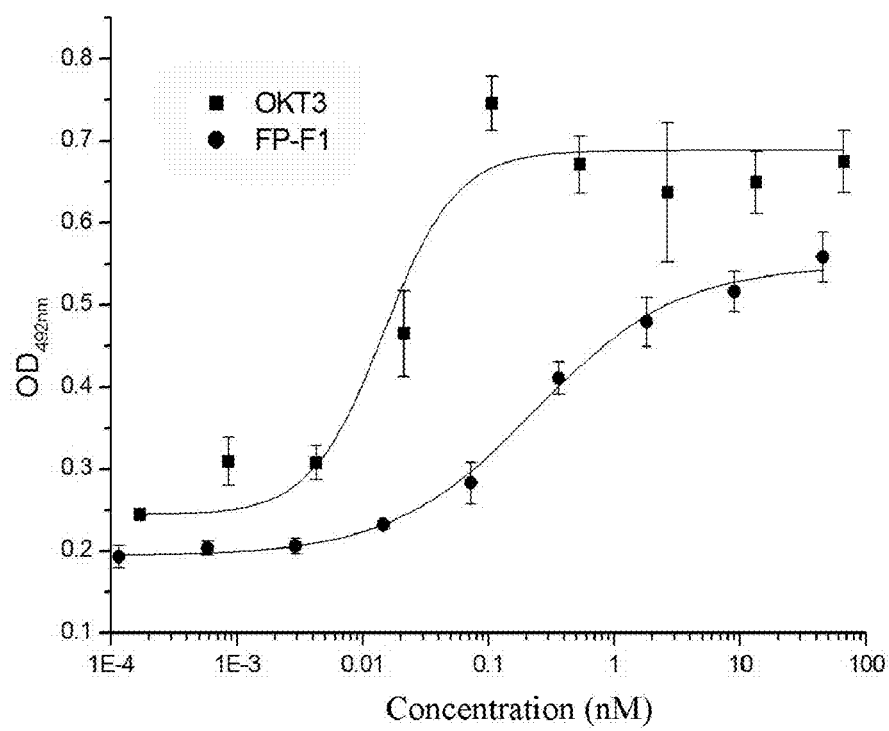
FIG. 16. The anti-CD3×CD20 bispecific antibody FP-F1 activated human PBMC cells in a concentration-dependent manner.

PBMCs were prepared from fresh human blood by density gradient centrifugation and resuspended at $5 \times 10^6$ cells/mL with medium containing 10% heat inactivated FBS for later use. The antibody (anti-CD3 monoclonal antibody OKT3 or bispecific antibody FP-F1) was diluted to 2 μg/mL using complete medium, and then diluted to 8 gradients at 1:5 ratio. The diluted antibody was added to a 96-well plate at 100 μL per well in triplicate. The medium was used as negative control and ConA was used as positive control. The PBMC cell suspension prepared as above was added to the 96-well plate at 100 μL/well, and cultured at 37° C., 5% $CO_2$ for 72 h. After incubation, the culture supernatant in the 96-well plate, 100 μL per well, was carefully aspirated, and the IFN-γ content in the supernatant was measured by an IFN-γ ELISA kit (BD Biosciences) (FIG. 15). 10 μL of the CCK-8 reagent was added to each well of the 96-well plate, and the incubation was continued for 4 h. Using the antibody concentration as the X-axis and the absorbance value at 492 nm as the Y-axis, a four-parameter S-curve was fitted and the $EC_{50}$ value was calculated (FIG. 16). The results showed that the amount of IFN-γ produced by FP-F1-activated T cells was positively correlated with the antibody concentration and slightly lower than that produced by the control antibody OKT3. This indicated that the anti-CD3 single chain antibody of the bispecific antibody functioned well. The $EC_{50}$ value that OKT3 activated human PBMCs was 0.015 nM, whereas that of FP-F1 was 0.233 nM. The activation ability of FP-F1 decreased by about two orders of magnitude, which helped to reduce the clinical toxicity of the bispecific antibody.

Another anti-CD3×CD20 bispecific antibody FP-F2 constructed in the present invention also activated T cells and produced IFN-γ in a concentration-dependent manner in the human PBMC cell activation assay. The $EC_{50}$ that FP-F2 activated human PBMCs was 0.214 nM, which was comparable to that of FP-F1.

7.3 Efficacy of Anti-CD3×CD20 Bispecific Antibody FP-F1 in Killing Subcutaneous Xenografts Human Burkitt's lymphoma Raji Cells (8×10⁶ cells, The Collection Cell Bank of Chinese Academy of Sciences) and Matrigel (BD Biosciences, Cat. No. 354234) were co-inoculated in female SCID Beige mice (Shanghai Lingchang Biotechnology Co., Ltd.) at a ratio of 1:1 subcutaneously. After 6 days of growth, the mice were grouped according to body weight and tumor volume, 7 mice per group. The cultured LAK cells were injected into the tumor tissue at a dose of 1×10⁶ cells/50 μL. Meantime, FP-F1 was administered in the same day at doses of 10, 1 and 0.1 mg/kg, respectively, twice a week by intravenous injection. The control groups were: (1) negative control group: solvent of FP-F1 (PBS); (2) positive control group: Rituxan® (anti-CD20 antibody, Genentech), administered at a dose of 10 mg/kg, twice a week by intravenous injection. The body weight and tumor volume of the mice were measured twice a week. The volume was calculated with ½×length×width×width (mm³).

Figure 17:
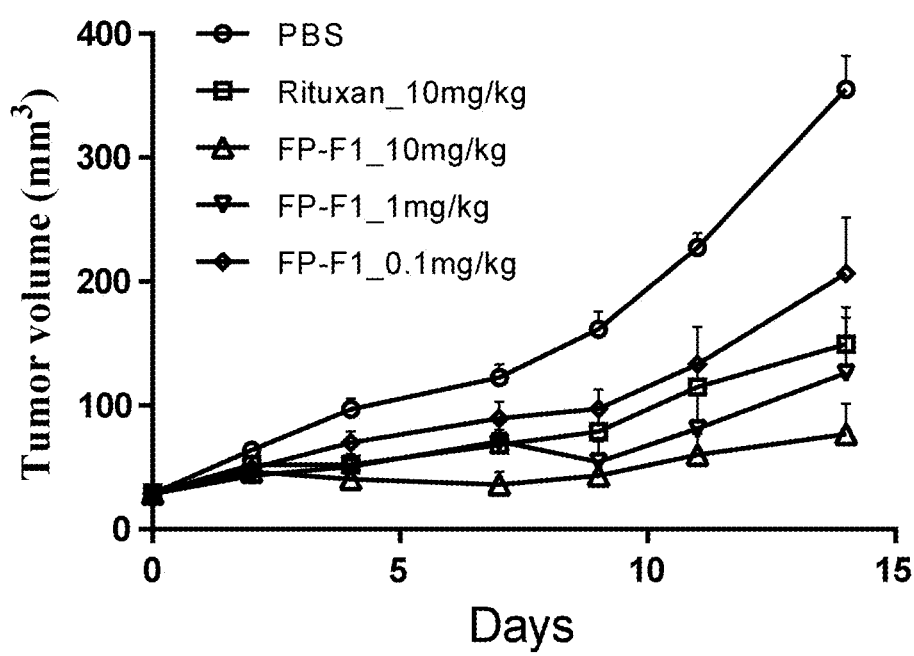
FIG. 17. The efficacy of anti-CD3×CD20 bispecific antibody FP-F1 in killing subcutaneous transplantation tumor.

In FIG. 17, different doses of FP-F1 showed good tumor growth-inhibition. The tumors in 2 mice in the 10 mg/kg group completely disappeared. The tumor in 1 mouse in the 1 mg/kg group had completely disappeared. The 0.1 mg/kg dose administered to one group also showed a certain effect of inhibiting tumor growth. The tumor in the negative control group grew normally and reached 400 mm³ on the 14th day. The results showed that the therapeutic effect of the 1 mg/kg FP-F1 dose was equivalent to that of the 10 mg/kg Rituxan dose, indicating that the effective dose of the bispecific antibody FP-F1 constructed in the present invention for inhibiting tumor growth in vivo was only ⅒ of that of the anti-CD20 monoclonal antibody (Rituxan®). It was expected that the clinical dose of FP-F1 would be greatly reduced.

All documents mentioned in the present invention are hereby incorporated by reference to the same extent as if each of the documents is individually recited for reference. It is to be understood that various changes and modifications may be made by those skilled in the art upon reading the above teachings of the present invention, which also fall within the scope of the claims appended hereto.

What is claimed is:

1. A fusion protein having the structural formula of K1-L-K2 or K2-L-K1, wherein L is a linker peptide between K1 and K2 and L comprises a flexible peptide and a rigid peptide, wherein the flexible peptide comprises one or more flexible units and the rigid peptide comprises one or more rigid units, wherein the flexible unit has the structural formula of (GS)a(GGS)b(GGGS)c(GGGGS)d (SEQ ID NO: 37), wherein each of a, b, c, and d is an integer equal to or more than 0, and a+b+c+d is selected from 4, 5, 6, and 8;

wherein the rigid unit comprises the amino acid sequence of SEQ ID NO: 1 or a fragment of SEQ ID NO: 1, wherein the fragment comprises the amino acid sequence of SEQ ID NO: 29 or the amino acid sequence of SEQ ID NO: 30; and wherein K1 or K2 each is selected from a protein, a protein domain, a peptide, an antibody, and an antigen-binding fragment of an antibody.

2. The fusion protein of claim 1, wherein the rigid unit comprises the at least two glycosylation sites.

3. The fusion protein of claim 1, wherein the rigid peptide comprises 1, 2, 3, 4, or 5 rigid units.

4. The fusion protein of claim 1, wherein the flexible unit comprises an amino acid sequence selected from:

i)
(SEQ ID NO: 21)
GSGGGGSGGGGSGGGGS;

ii)
(SEQ ID NO: 22)
GSGGGGSGGGGSGGGGSGGGGSGGGGS;

iii)
(SEQ ID NO: 23)
GSGGGGSGGGGSGGGGSGGGGSGGGGSGGGGSGGGGS;

iv)
(SEQ ID NO: 24)
GSGGGGSGGGGSGGGGS;

v)
(SEQ ID NO: 25)
GGGSGGGSGGGSGGGSGGGS;
and vi)
(SEQ ID NO: 26)
GGSGGSGGSGGS.

5. The fusion protein of claim 3, wherein the rigid unit comprises an amino acid sequence selected from:

i)
(SEQ ID NO: 27)
SSSSKAPPPSLPSPSRLPGPSDTPILPQ;

ii)
(SEQ ID NO: 28)
PRFQDSSSSKAPPPSLPSPSRLPGPSDTPILPQ;

iii)
(SEQ ID NO: 29)
SSSSKAPPPS;

iv)
(SEQ ID NO: 30)
SRLPGPSDTPILPQ;
and v)
(SEQ ID NO: 31)
SSSSKAPPPSLPSPSR.

6. The fusion protein of claim 1, wherein L comprises an amino acid sequence of SEQ ID NO: 2.

7. The fusion protein of claim 1, wherein L comprises an amino acid sequence of SEQ ID NO: 3.

8. The fusion protein of claim 1, wherein L comprises an amino acid sequence of SEQ ID NO: 4.

9. The fusion protein of claim 1, wherein L comprises an amino acid sequence of SEQ ID NO: 5.

10. The fusion protein of claim 1, wherein L comprises an amino acid sequence of SEQ ID NO: 6.

11. The fusion protein of claim 1, wherein L comprises an amino acid sequence of SEQ ID NO: 7.

12. The fusion protein of claim 1, wherein K1 is a soluble or membrane signal molecule, a cytokine, a growth factor, a hormone, a costimulatory molecule, an enzyme, a receptor, or a protein or peptide which is a ligand to a receptor, and wherein K2 is a protein or a protein domain which prolongs the circulation half-life of K1.

13. The fusion protein of claim 12, wherein K2 is selected from a human hemoglobin, an iron Transferrin, and an Fc fragment of an immunoglobulin.

14. The fusion protein of claim 11, wherein K1 is selected from a toxin, an enzyme, a cytokine, a membrane protein, and an immunoregulatory cytokine; K2 is an antibody or an antigen-binding fragment thereof; and K1 is connected to K2 via L to form an antibody fusion protein.

15. The fusion protein of claim 1, wherein K1 is selected from an adenosine A1 receptor, angiotensin-converting enzyme (ACE), Activin family, ADAM family, ALK family, α-1-antitrypsin, programmed cell death protein family, nerve growth factor and receptor family, bone morphogenetic protein (BMP) and receptor family, complement factor, calcitonin, cancer associated antigen, cathepsin family, CCL chemokine and receptor family, CD superfamily, CFTR, CXCL chemokine and receptor family, EGF and receptor family, blood coagulation factor IIa, factor VII, VIII, IX, ferritin, fibroblast growth factor (FGF) and receptor family, follicle stimulating hormone, FZD family, HGF, glucagon, Cardiac myosin, growth hormone, Ig, IgA receptor, IgE, insulin-like growth factor (IGF) and binding protein family, interleukin (IL) and receptor superfamily, interferon (INF) family, iNOS, integrin family, kallikrein protein family, laminin, L-selectin, luteinizing hormone, MMP family, mucin-like family, cadherin superfamily, platelet-derived growth factor (PDGF) and receptor family, parathyroid hormone, serum albumin, T-cell receptor superfamily, TGF-α, transforming growth factor-β superfamily, thyroid stimulating hormone, parathyroid stimulating hormone, tumor necrosis factor (TNF) superfamily and receptor TNFRSF superfamily, urokinase, WNT signaling pathway family, thymosin a1, thymosin β4, and VEGF and receptor family.

16. The fusion protein of claim 1, wherein L has an amino acid sequence of any one of SEQ ID NOs: 2-7, K2 comprises an amino acid sequence of any one of SEQ ID NOs: 8-12, and wherein K1 is Exendin-4 having the amino acid sequence of SEQ ID NO: 15.

17. A method for the treatment of type II (non-insulin dependent) diabetes, comprising administering an effective amount of the fusion protein of claim 16 to a subject suffering from type II (non-insulin dependent) diabetes.

18. A method for the treatment of obesities, comprising administering an effective amount of the fusion protein of claim 16 to a subject suffering from obesities.

19. The fusion protein of claim 1, wherein L has an amino acid sequence of any one of SEQ ID NOs: 2-7, K1 is human coagulation factor VII (FVII) having the amino acid sequence of SEQ ID NO: 13, human coagulation factor VIII (FVIII) having the amino acid sequence of SEQ ID NO: 14, interleukin IL-7 having the amino acid sequence of SEQ ID NO: 16, or human growth factor having the amino acid sequence of SEQ ID NO: 17, and K2 comprises an amino acid sequence of any one of SEQ ID NOs: 8-12.

20. The fusion protein of claim 1, wherein K1 is a double chain antibody of anti-CD20; K2 is a single chain antibody of anti-CD3, and K1 is connected to K2 by L to form a bispecific antibody, wherein the linker peptide comprises an amino acid sequence selected from SEQ ID NOs: 2-7, K1 comprises a heavy chain having the amino acid sequence of SEQ ID NO: 18 and a light chain having the amino acid sequence of SEQ ID NO: 19; and K2 comprises the amino acid sequence of SEQ ID NO: 20.

* * * * *

SEQUENCE LISTING

```
<160> NUMBER OF SEQ ID NOS: 38

<210> SEQ ID NO 1
<211> LENGTH: 33
<212> TYPE: PRT
<213> ORGANISM: Homo sapiens

<400> SEQUENCE: 1

Pro Arg Phe Gln Asp Ser Ser Ser Lys Ala Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 2
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Peptide Linker F2-R1

<400> SEQUENCE: 2

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Ser Ser Ser Ser Lys
            20                  25                  30

Ala Pro Pro Pro Ser Leu Pro Ser Pro Ser Arg Leu Pro Gly Pro Ser
        35                  40                  45
```

Asp Thr Pro Ile Leu Pro Gln
        50                  55

<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Peptide Linker F1-R2

<400> SEQUENCE: 3

Gly Ser Gly Gly Gly Ser Gly Gly Gly Ser Gly Gly Gly Ser
1               5                   10                  15

Pro Arg Phe Gln Asp Ser Ser Ser Lys Ala Pro Pro Ser Leu
            20                  25                  30

Pro Ser Pro Ser Arg Leu Pro Gly Pro Ser Asp Thr Pro Ile Leu Pro
        35                  40                  45

Gln

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Peptide Linker F4-R1

<400> SEQUENCE: 4

Gly Ser Gly Gly Gly Ser Gly Gly Gly Ser Gly Gly Gly Gly
1               5                   10                  15

Ser Ser Ser Ser Ser Lys Ala Pro Pro Pro Ser Leu Pro Ser Pro Ser
            20                  25                  30

Arg Leu Pro Gly Pro Ser Asp Thr Pro Ile Leu Pro Gln
        35                  40                  45

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Peptide Linker F5-R5

<400> SEQUENCE: 5

Gly Gly Gly Ser Gly Gly Gly Ser Gly Gly Gly Ser Gly Gly Gly Ser
1               5                   10                  15

Gly Gly Gly Ser Ser Ser Ser Ser Lys Ala Pro Pro Ser Leu Pro
            20                  25                  30

Ser Pro Ser Arg
        35

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic

```
                           polypeptide
<220> FEATURE:
<223> OTHER INFORMATION: Amino Acid Sequence of Peptide Linker F4-R3R3

<400> SEQUENCE: 6

Gly Ser Gly Gly Gly Ser Gly Gly Gly Ser Gly Gly Gly
1               5                   10                  15

Ser Ser Ser Ser Ser Lys Ala Pro Pro Ser Ser Ser Ser Lys
                20                  25                  30

Ala Pro Pro Ser
        35

<210> SEQ ID NO 7
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Peptide Linker F6-R4R4R4

<400> SEQUENCE: 7

Gly Gly Ser Gly Gly Ser Gly Gly Ser Gly Gly Ser Ser Arg Leu Pro
1               5                   10                  15

Gly Pro Ser Asp Thr Pro Ile Leu Pro Gln Ser Arg Leu Pro Gly Pro
                20                  25                  30

Ser Asp Thr Pro Ile Leu Pro Gln Ser Arg Leu Pro Gly Pro Ser Asp
        35                  40                  45

Thr Pro Ile Leu Pro Gln
    50

<210> SEQ ID NO 8
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of vFc gamma 1

<400> SEQUENCE: 8

Asp Lys Thr His Thr Cys Pro Pro Cys Pro Ala Pro Glu Val Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 9
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of vFc gamma 2-1

<400> SEQUENCE: 9

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 10
<211> LENGTH: 223
<212> TYPE: PRT
<213> ORGANISM: Artificial Sequence -continued

```
<220> FEATURE:
<223> OTHER INFORMATION: Description of Artificial Sequence: Synthetic
      polypeptide
<220> FEATURE:
<223> OTHER INFORMATION: Amino Acid Sequence of vFc gamma 2-2

<400> SEQUENCE: 10

Val Glu Cys Pro Pro Cys Pro Ala Pro Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 11
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of vFc gamma 2-3

<400> SEQUENCE: 11

Val Glu Cys Pro Pro Cys Pro Ala Pro Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
```

```
                    85                  90                  95
Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 12
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of vFc gamma 4

<400> SEQUENCE: 12

Glu Ser Lys Tyr Gly Pro Pro Cys Pro Pro Cys Pro Ala Pro Glu Phe
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
```

Leu Ser Leu Gly Lys
225

<210> SEQ ID NO 13
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Mature FVII Protein

<400> SEQUENCE: 13

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser

```
                      325                 330                 335
Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
                355                 360                 365

Ala Thr Val Gly His Phe Gly Val Tyr Thr Arg Val Ser Gln Tyr Ile
            370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 14
<211> LENGTH: 1438
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Mature FVIII Protein

<400> SEQUENCE: 14

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
```

```
            260                 265                 270
Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685
```

-continued

```
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Val Leu Lys Arg His
            740                 745                 750
Gln Arg Glu Ile Thr Arg Thr Leu Gln Ser Asp Gln Glu Ile
                755                 760                 765
Asp Tyr Asp Asp Thr Ile Ser Val Glu Met Lys Lys Gly Asp Phe Asp
770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
                835                 840                 845
Phe Thr Gln Pro Leu Tyr Arg Gly Glu Leu Asn Glu His Leu Gly Leu
850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
                915                 920                 925
Met Ala Pro Thr Lys Asp Glu Phe Asp Cys Lys Ala Trp Ala Tyr Phe
930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
                980                 985                 990
Lys Ser Trp Tyr Phe Thr Glu Asn Met Glu Arg Asn Cys Arg Ala Pro
                995                 1000                1005
Cys Asn Ile Gln Met Glu Asp Pro Thr Phe Lys Glu Asn Tyr Arg
    1010                1015                1020
Phe His Ala Ile Asn Gly Tyr Ile Met Asp Thr Leu Pro Gly Leu
    1025                1030                1035
Val Met Ala Gln Asp Gln Arg Ile Arg Trp Tyr Leu Leu Ser Met
    1040                1045                1050
Gly Ser Asn Glu Asn Ile His Ser Ile His Phe Ser Gly His Val
    1055                1060                1065
Phe Thr Val Arg Lys Lys Glu Glu Tyr Lys Met Ala Leu Tyr Asn
    1070                1075                1080
Leu Tyr Pro Gly Val Phe Glu Thr Val Glu Met Leu Pro Ser Lys
    1085                1090                1095
```

```
Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 15
<211> LENGTH: 39
<212> TYPE: PRT
<213> ORGANISM: Heloderma suspectum

<400> SEQUENCE: 15

His Gly Glu Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 16
<211> LENGTH: 152
<212> TYPE: PRT
<213> ORGANISM: Homo sapiens

<400> SEQUENCE: 16

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 17
<211> LENGTH: 191
<212> TYPE: PRT
<213> ORGANISM: Homo sapiens

<400> SEQUENCE: 17

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

```
Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 18
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of the Heavy Chain of Anti-
      CD20 Antibody

<400> SEQUENCE: 18

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                 295                 300
Arg Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of the Light Chain of
      Anti-CD20 antibody

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 20
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Anti-CD3 scFv

<400> SEQUENCE: 20

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
    210                 215                 220

Ser Ser Asn Pro Phe Thr Phe Gly Gln Gly Thr Lys Leu Gln Ile Thr
225                 230                 235                 240

Arg
```

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of flexible unit F1

```
<400> SEQUENCE: 21

Gly Ser Gly Gly Gly Ser Gly Gly Gly Ser Gly Gly Gly Gly Ser
1               5                   10                  15

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of flexible unit F2

<400> SEQUENCE: 22

Gly Ser Gly Gly Gly Gly Ser Gly Gly Gly Gly Ser Gly Gly Gly
1               5                   10                  15

Ser Gly Gly Gly Gly Ser Gly Gly Gly Gly Ser
            20                  25

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of flexible unit F3

<400> SEQUENCE: 23

Gly Ser Gly Gly Gly Gly Ser Gly Gly Gly Gly Ser Gly Gly Gly
1               5                   10                  15

Ser Gly Gly Gly Gly Ser Gly Gly Gly Gly Ser Gly Gly Gly Ser
            20                  25                  30

Gly Gly Gly Gly Ser
        35

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Flexible Unit F4

<400> SEQUENCE: 24

Gly Ser Gly Gly Gly Gly Ser Gly Gly Gly Gly Ser Gly Gly Gly Gly
1               5                   10                  15

Ser

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Flexibile Unit F5

<400> SEQUENCE: 25

Gly Gly Gly Ser Gly Gly Gly Ser Gly Gly Gly Ser Gly Gly Gly Ser
```

```
1               5                   10                  15

Gly Gly Gly Ser
            20

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Flexible Unit F6

<400> SEQUENCE: 26

Gly Gly Ser Gly Gly Ser Gly Gly Ser Gly Gly Ser
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Rigid Unit R1

<400> SEQUENCE: 27

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Rigid Unit R2

<400> SEQUENCE: 28

Pro Arg Phe Gln Asp Ser Ser Ser Ser Lys Ala Pro Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Rigid Unit R3

<400> SEQUENCE: 29

Ser Ser Ser Ser Lys Ala Pro Pro Pro Ser
1               5                   10

<210> SEQ ID NO 30
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Rigid Unit R4

<400> SEQUENCE: 30

Ser Arg Leu Pro Gly Pro Ser Asp Thr Pro Ile Leu Pro Gln
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Rigid Unit R5

<400> SEQUENCE: 31

Ser Ser Ser Ser Lys Ala Pro Pro Pro Ser Leu Pro Ser Pro Ser Arg
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Amino Acid Sequence of Rigid Peptide R3-R3

<400> SEQUENCE: 32

Ser Ser Ser Ser Lys Ala Pro Pro Pro Ser Ser Ser Ser Lys Ala
1               5                   10                  15

Pro Pro Pro Ser
            20

<210> SEQ ID NO 33
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino Acid Sequence of Rigid Peptide R4-R4-R4

<400> SEQUENCE: 33

Ser Arg Leu Pro Gly Pro Ser Asp Thr Pro Ile Leu Pro Gln Ser Arg
1               5                   10                  15

Leu Pro Gly Pro Ser Asp Thr Pro Ile Leu Pro Gln Ser Arg Leu Pro
            20                  25                  30

Gly Pro Ser Asp Thr Pro Ile Leu Pro Gln
            35                  40

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 34

Ala Glu Ala Ala Ala Lys Ala
1               5

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Thr Ser Gly Ser Gly Lys Ser Ser Glu Gly Lys Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MISC_FEATURE
<222> LOCATION: (3)..(5)
<223> OTHER INFORMATION: May or may not be present
<220> FEATURE:
<221> NAME/KEY: MISC_FEATURE
<222> LOCATION: (6)..(9)
<223> OTHER INFORMATION: May or may not be present
<220> FEATURE:
<221> NAME/KEY: MISC_FEATURE
<222> LOCATION: (10)..(14)
<223> OTHER INFORMATION: May or may not be present
<220> FEATURE:
<223> OTHER INFORMATION: See specification as filed for detailed
      description of substitutions and preferred embodiments

<400> SEQUENCE: 37

Gly Ser Gly Gly Ser Gly Gly Gly Ser Gly Gly Gly Gly Ser
1               5                   10

```
<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Gly Ser
1               5
```